(12) United States Patent
Bruce et al.

(10) Patent No.: US 7,780,614 B2
(45) Date of Patent: Aug. 24, 2010

(54) ORTHOPEDIC SUPPORTS AND METHOD OF USING SAME

(75) Inventors: Lloyd Bruce, Cincinnati, OH (US); Sherry Hinds, Goshen, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 254 days.

(21) Appl. No.: 11/620,932

(22) Filed: Jan. 8, 2007

(65) Prior Publication Data

US 2007/0197944 A1 Aug. 23, 2007

Related U.S. Application Data

(60) Provisional application No. 60/757,244, filed on Jan. 9, 2006.

(51) Int. Cl.
*A61F 5/00* (2006.01)
(52) U.S. Cl. .................................................. 602/20
(58) Field of Classification Search ............... 602/5, 602/20–23, 26–27; 128/882; 2/16
See application file for complete search history.

(56) References Cited

U.S. PATENT DOCUMENTS

| | | | | |
|---|---|---|---|---|
| 5,168,577 A | * | 12/1992 | Detty | 2/16 |
| 5,474,524 A | * | 12/1995 | Carey | 602/26 |
| 5,899,872 A | * | 5/1999 | Gilmour | 602/65 |
| 5,944,678 A | * | 8/1999 | Hubbard | 602/27 |
| D454,199 S | | 3/2002 | Lamping et al. | |
| 6,582,382 B2 | * | 6/2003 | Domanski et al. | 602/1 |
| 2003/0050586 A1 | | 3/2003 | Domanski et al. | |

* cited by examiner

*Primary Examiner*—Michael A. Brown
(74) *Attorney, Agent, or Firm*—Lisa P. Fulton

(57) ABSTRACT

An orthopedic support for supporting a joint of a wearer is provided and includes a sheet of flexible laminate material configured to at least partially enclose the joint. The orthopedic support also includes a spacer material attached to the sheet of material about at least a portion of its outer periphery, and at least one strap integrally defined in the sheet of material and configured to tension and secure the sheet of material about the wearer's joint.

21 Claims, 24 Drawing Sheets

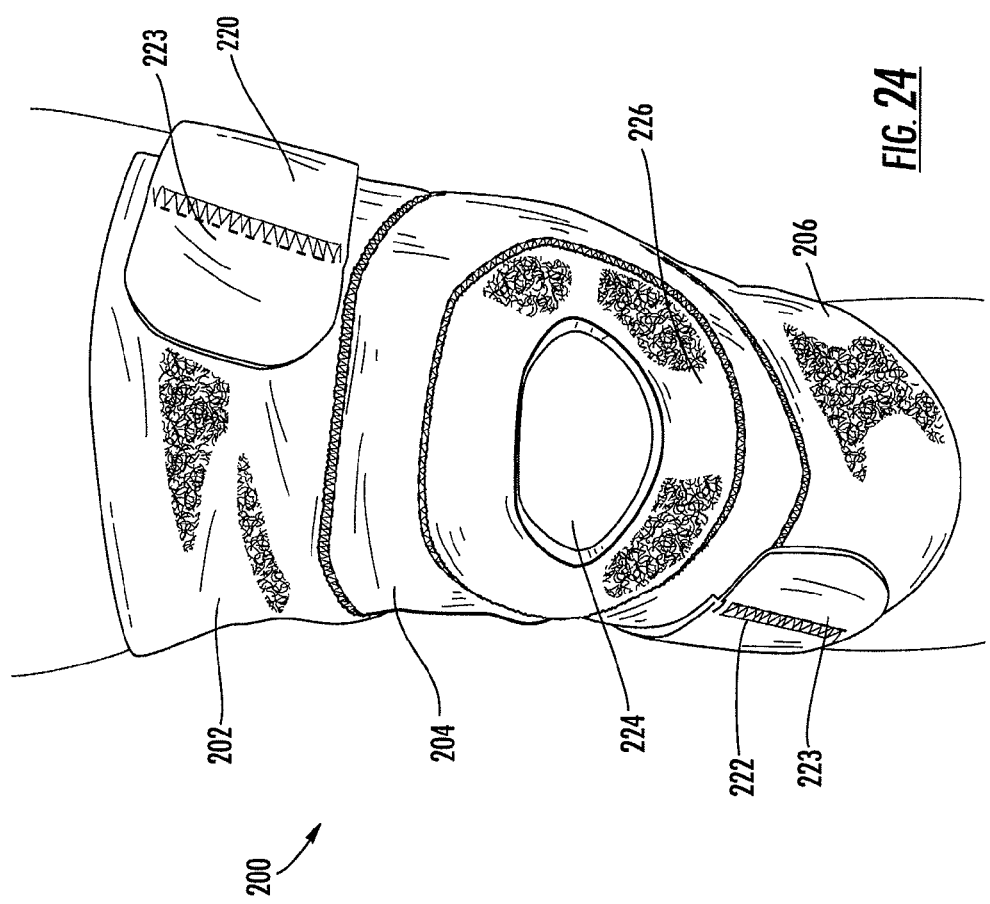

ORTHOPEDIC SUPPORTS AND METHOD OF USING SAME

CROSS-REFERENCE TO RELATED APPLICATIONS

The present application claims priority from U.S. Provisional Application No. 60/757,244 filed Jan. 9, 2006, the contents of which are incorporated herein by reference.

BACKGROUND OF THE INVENTION

1. Field of the Invention

The present invention is related to the field of orthopedic supports, and more particularly, to orthopedic supports having a laminate construction and various strapping configurations for increased comfort and support.

2. Description of Related Art

Various materials have been developed for use with orthopedic supports. For example, textiles, open cell and closed cell foams, neoprene, etc. have been used independently or in combination as a laminate where two or more layers of material are positioned adjacent to one another. The type of materials, material properties, and thicknesses may be varied to achieve, among other properties, a desired amount of support, elasticity, cushioning, breathability, and bulkiness.

One example of a laminate material is disclosed in U.S. Pat. No. 5,139,477 to Peters. The '477 patent discloses a knee sleeve having a laminate material of an open-cell foam core sandwiched between an outer layer of elasticized fabric having a looped structure, and an inner layer of elasticized cotton fabric. In particular, the outer layer includes a blend of inelastic (e.g., polyamides) and elastomeric (e.g., polyurethane) fibers, while the inner layer includes a blend of cotton and elastomeric fibers.

Furthermore, various strapping configurations may be defined in the laminate material or otherwise attached thereto, and the base laminate material may be engageable with one or more fasteners on the ends of the straps. For instance, the '477 patent discloses that the knee sleeve includes integral encircling straps that have hook fasteners that mate with looped fasteners on the outer surface of the outer layer. The encircling straps are preferably of sufficient length to encircle the entire calf or thigh but typically 1½ times so that respective straps may double back on themselves.

Despite these improvements in materials and strapping configurations for orthopedic supports, additional innovations are needed. In particular, materials providing increased comfort and breathability without sacrificing mobility or bulkiness of the support are needed. In particular, although techniques have been developed to secure orthopedic supports to a wearer's limb, there is a need for fasteners and a strapping system that more effectively secure the support to the wearer's limb and are more economical and efficient to manufacture. Furthermore, techniques are needed to more easily position, secure, and readjust an orthopedic support on a wearer's limb.

It would therefore be advantageous to provide an orthopedic support that includes a laminate material promoting comfort without sacrificing mobility. In addition, it would be advantageous to provide an orthopedic support that includes various strapping systems that may be easily manufactured and used for various orthopedic applications.

BRIEF SUMMARY OF THE INVENTION

The present invention addresses the above needs and achieves other advantages by providing an orthopedic support for supporting a portion of a limb of the wearer. The orthopedic support generally includes a sheet of flexible laminate material for conforming to a portion of the wearer's anatomy, as well as straps for securing the laminate material on the wearer. The laminate material provides improved comfort and moisture-wicking properties, while the straps provide a unique configuration that reduces assembly time and adequately secures the support to the limb of the wearer.

An orthopedic support for supporting a joint of a wearer is provided and includes a sheet of flexible laminate material configured to at least partially enclose the joint. The sheet of flexible laminate material comprises an inner layer of stretch fleece material, an outer layer of stretch unbroken loop material, and a layer of stretch polyurethane foam positioned between the inner and outer layers of material. The sheet includes proximal and distal edges that are configured to encircle at least a portion of the wearer's limb. The stretch fleece could be configured in a grid pattern, while the unbroken loop material could include a plurality of eyelets. The support also includes at least one strap, where at least one strap is defined along at least one of the distal and proximal edges of the sheet of material, and each strap is configured to attach to the outer layer so as to secure the sheet of material about the joint.

The sheet of flexible laminate material, according to one variation of the orthopedic support, includes lateral edges attached to one another to define a sleeve. The sleeve includes a proximal edge defining a proximal opening and a distal edge defining a distal opening, wherein the limb of the wearer extends through the proximal and distal openings during use. In addition, the orthopedic support may include straps defined integrally with the sheet of material. For example, one strap may be defined integrally along a portion of the proximal edge, while a second strap may be defined integrally along a portion of the distal edge. At least a pair of the plurality of straps could extend laterally from the sheet of material in the same direction or in opposite directions. Moreover, the orthopedic support may include a tab integrally defined along the distal edge, opposite a respective strap, such that the strap may extend over the tab and attach to the outer layer of material.

Furthermore, variations of the orthopedic support include a spacer material. For instance, the spacer material could be textile material such as a three-dimensional knit fabric that enhances breathability in areas of joint bending. The spacer material could be attached to the sheet of flexible laminate material at various locations. For example, the spacer material could be located in a region proximate to bending of the joint, where the spacer material provides material properties for enhanced comfort and/or support. The spacer material could be configured to extend partially about the joint or about the entire circumference of the joint and may be various configurations, such as having holes for increasing breathability.

In one embodiment of the present invention, the orthopedic support is a knee support. The knee support typically includes a patellar opening for accommodating the patella of the wearer. In one embodiment, the knee support includes an eye-shaped patellar portion, where the patellar opening is defined therein. The eye-shaped portion is attached to the flexible laminate sheet of material along two spiral lateral edges extending between the proximal and distal edges. The eye-shaped portion is also a laminate material.

In a further embodiment of the present invention, the orthopedic support is an ankle support comprising a flexible laminate sheet of material, as discussed above. The ankle support may include a pair of opposed straps defined along the distal edge, and a strap defined along the proximal edge. The distal straps are capable of extending from under the instep of the foot, crossing over one another, and attaching to the outer layer proximate to the ankle. The ankle support could also include a tab defined along the proximal edge, opposite the proximal strap, wherein the proximate strap is configured to extend over the tab and attach to the outer layer. Moreover, the ankle support may include an opening defined in the sheet of flexible laminate material for accommodating a heel of the wearer. The ankle support could also include a sheet of material attached to the inner layer to define a sleeve. Furthermore, the ankle support may include a spacer material. The spacer material, such as three-dimensional spacer fabric, could be positioned to extend from the wearer's heel and along the Achilles tendon. The spacer material could include a plurality of holes defined therein.

Another embodiment of the present invention provides an ankle support that includes a sheet of flexible laminate material, as described above. The ankle support includes a pair of straps integrally defined in the sheet of material. According to one aspect of the ankle support, one strap is integrally defined along a proximal edge of the sheet of material, while a second strap is integrally defined along a distal edge of the sheet of material. The ankle support also includes a tab defined along the proximal edge, opposite the proximal strap, such that the proximal strap may extend over the tab and attach to the outer material.

The ankle support is configured in a single sheet of flexible laminate material having distal and proximal ends. The ankle support is bifurcated approximately the midpoint of the sheet of material. A portion of the distal end is attached to the distal edge, while the remaining portion of the distal end defines the distal strap. Similarly, a portion of the proximal end is attached to the proximal edge, while the remaining portion of the proximal end defines the proximal strap. As such, the proximal and distal ends are attached to the sheet of material in a spiral configuration to define a sleeve. Furthermore, the proximal and distal ends are attached to the sheet of material to define an opening for accommodating a heel of a wearer.

The present invention has many advantages. For instance, the orthopedic supports provide a unique combination of materials that promote increased comfort and moisture-wicking properties. In particular, each of the materials is stretchable, which allows the support to conform to various limb sizes, as well as breathable for wicking moisture away from the skin to provide increased comfort over prolonged periods of use. The orthopedic support may incorporate spacer materials to provide further comfort in the areas of joint bending, such as in the popliteal region of the knee. Furthermore, the orthopedic supports are capable of being configured for supporting a variety of limbs, such as the knee and ankle, and include unique strapping configurations for securing each support to the wearer's limb. In addition, the supports may be formed from a single sheet of material, which reduces the time and the number of components required for assembly.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 24 is a perspective view of the knee support shown in FIGS. 22 and 23 positioned on a wearer's knee.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Generally, the present invention provides an orthopedic support that includes a sheet of flexible laminate material for wrapping about and conforming to a portion of a wearer's anatomy. One or more straps are configured for securing the sheet of material about the wearer's anatomy. The orthopedic support could be worn on a limb or portions of a limb of a wearer, such as, for example, on a wrist, knee, ankle, elbow, back, arm, forearm, leg, or thigh.

Figure 3:
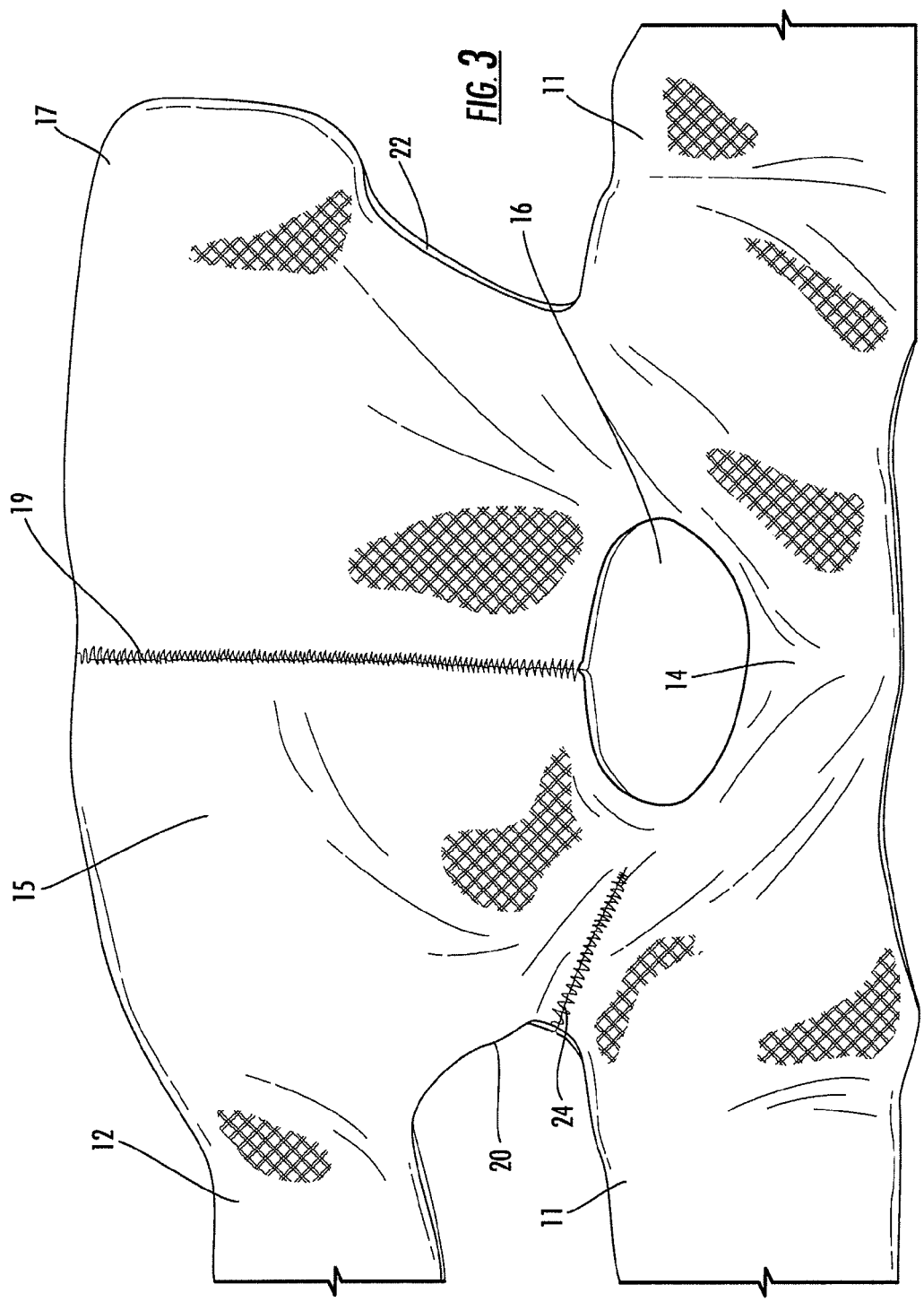
FIG. 3 is an enlarged plan view of the inner surface of the ankle support shown in FIG. 1.
Figure 4:
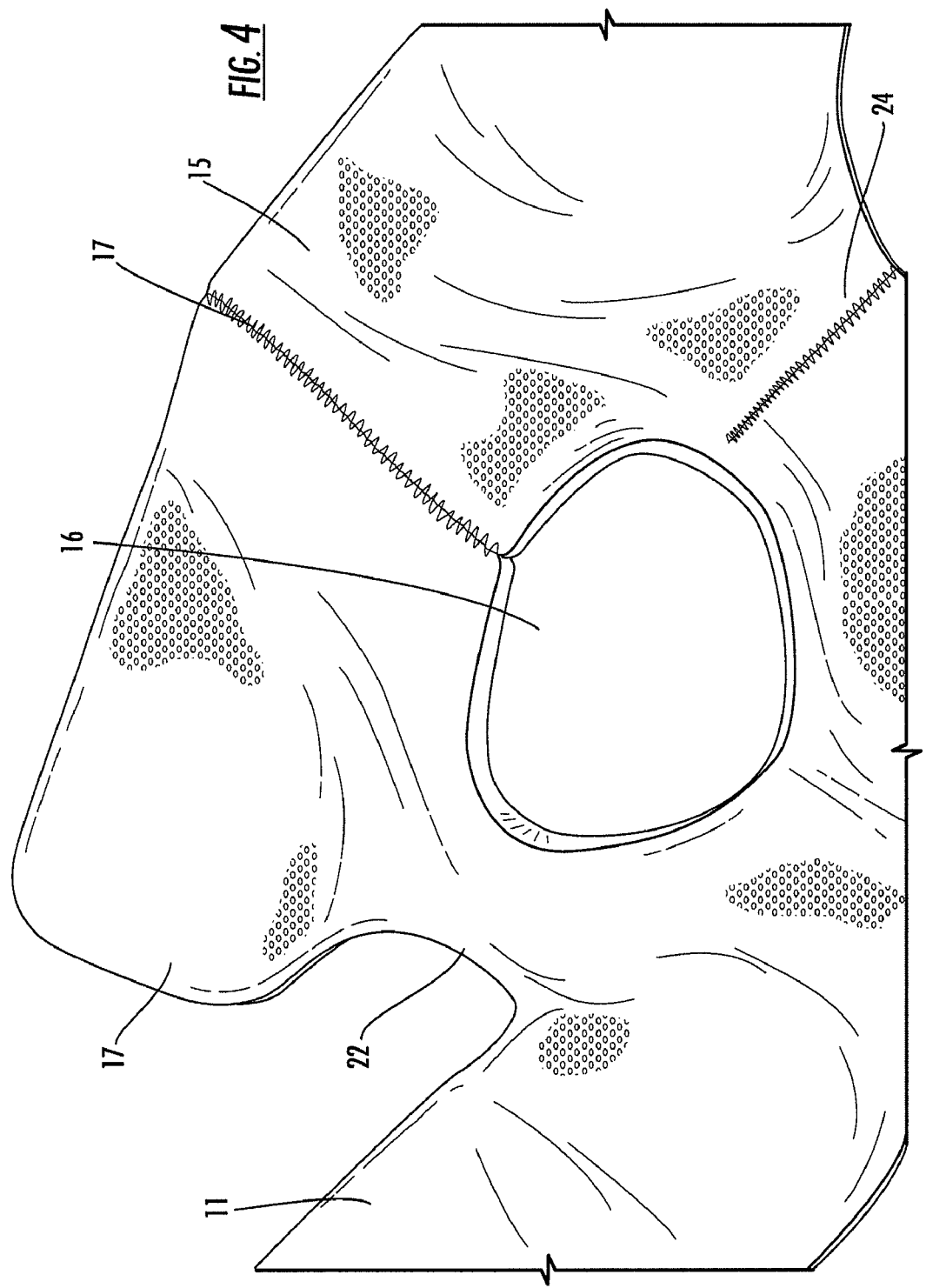
FIG. 4 is an enlarged plan view of the outer surface of the ankle support shown in FIG. 2.
Figure 5:
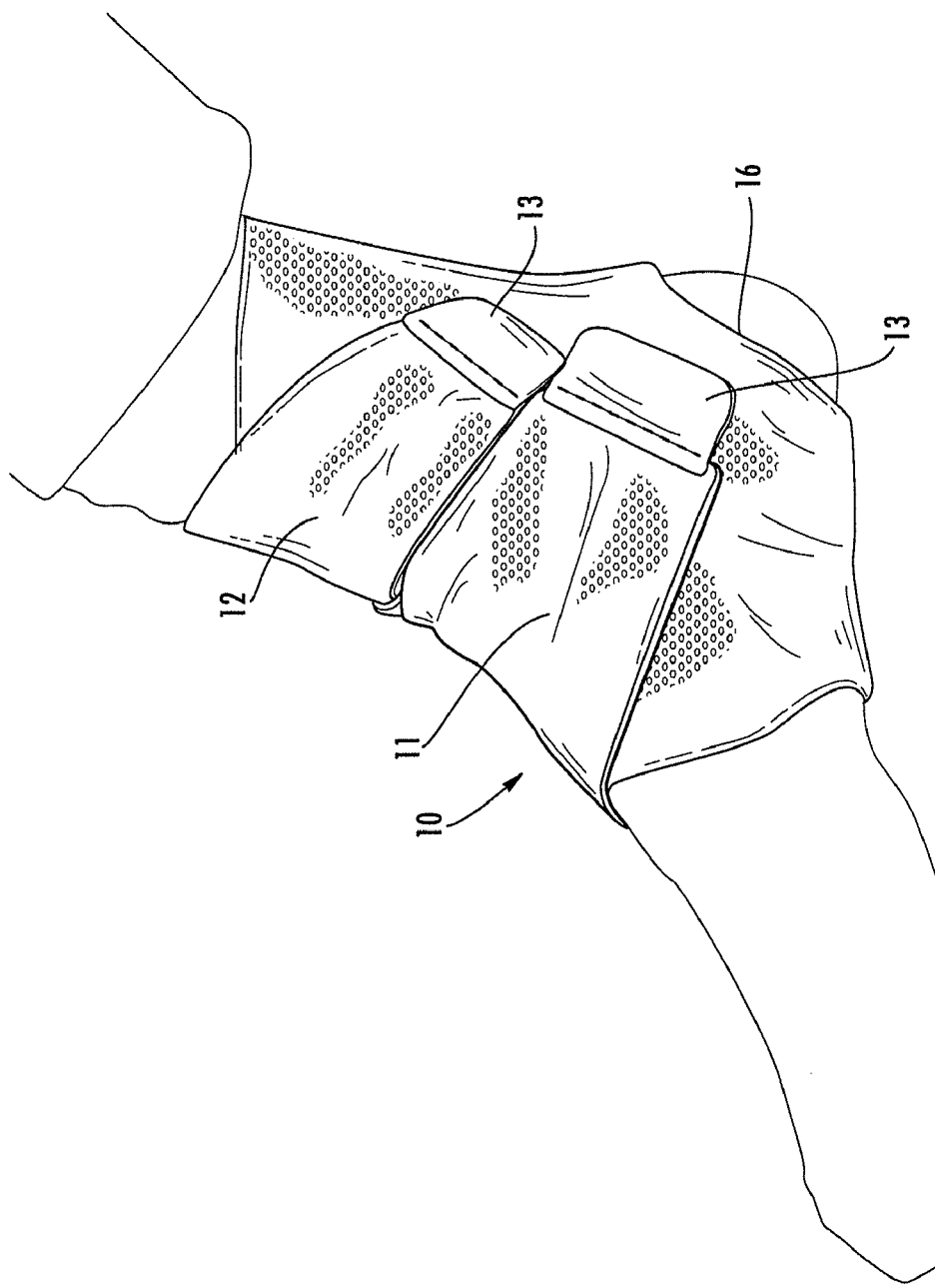
FIGS. 5 and 6 are perspective views of the ankle support of FIG. 1 positioned on a wearer's ankle.
Figure 6:
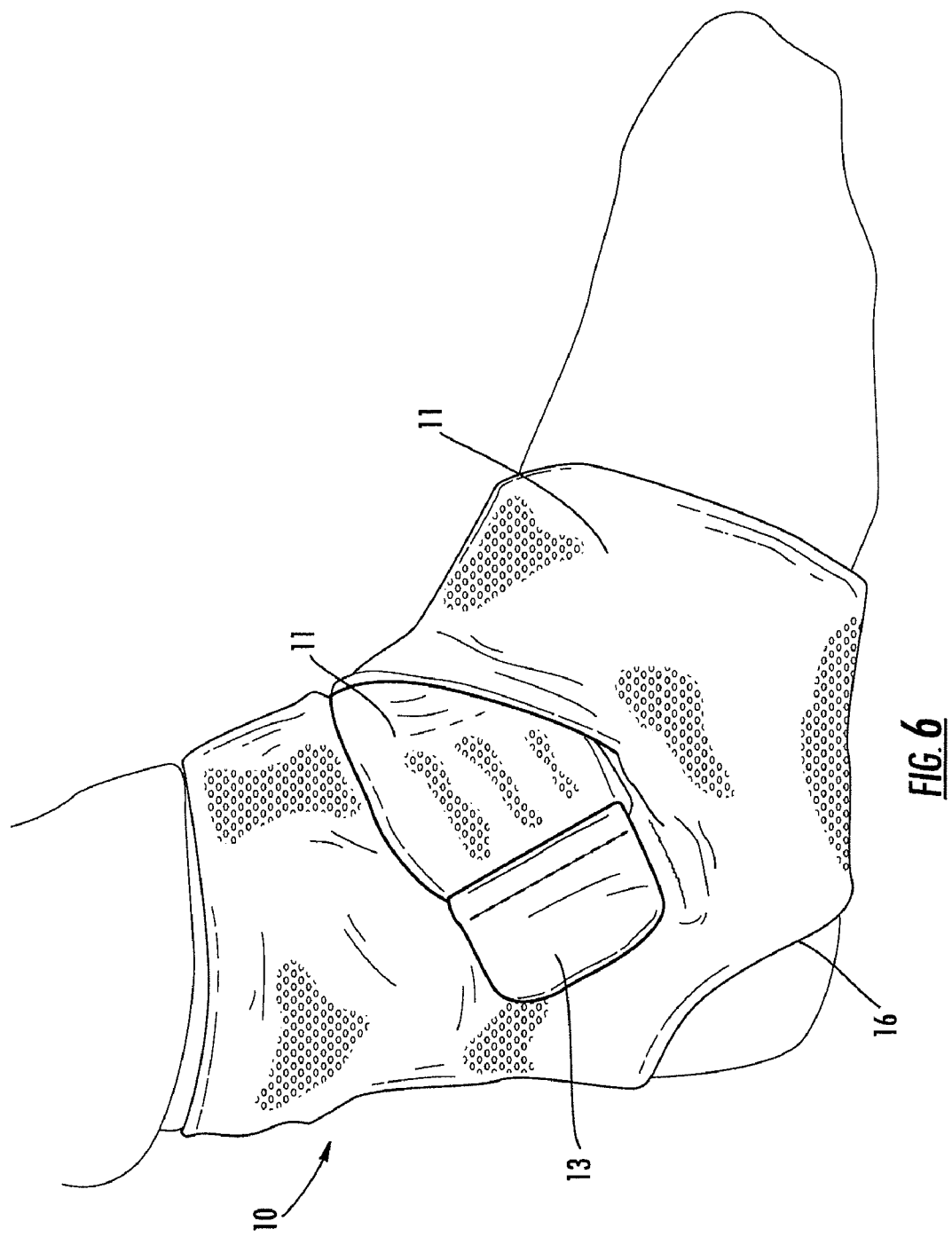
Figure 7:
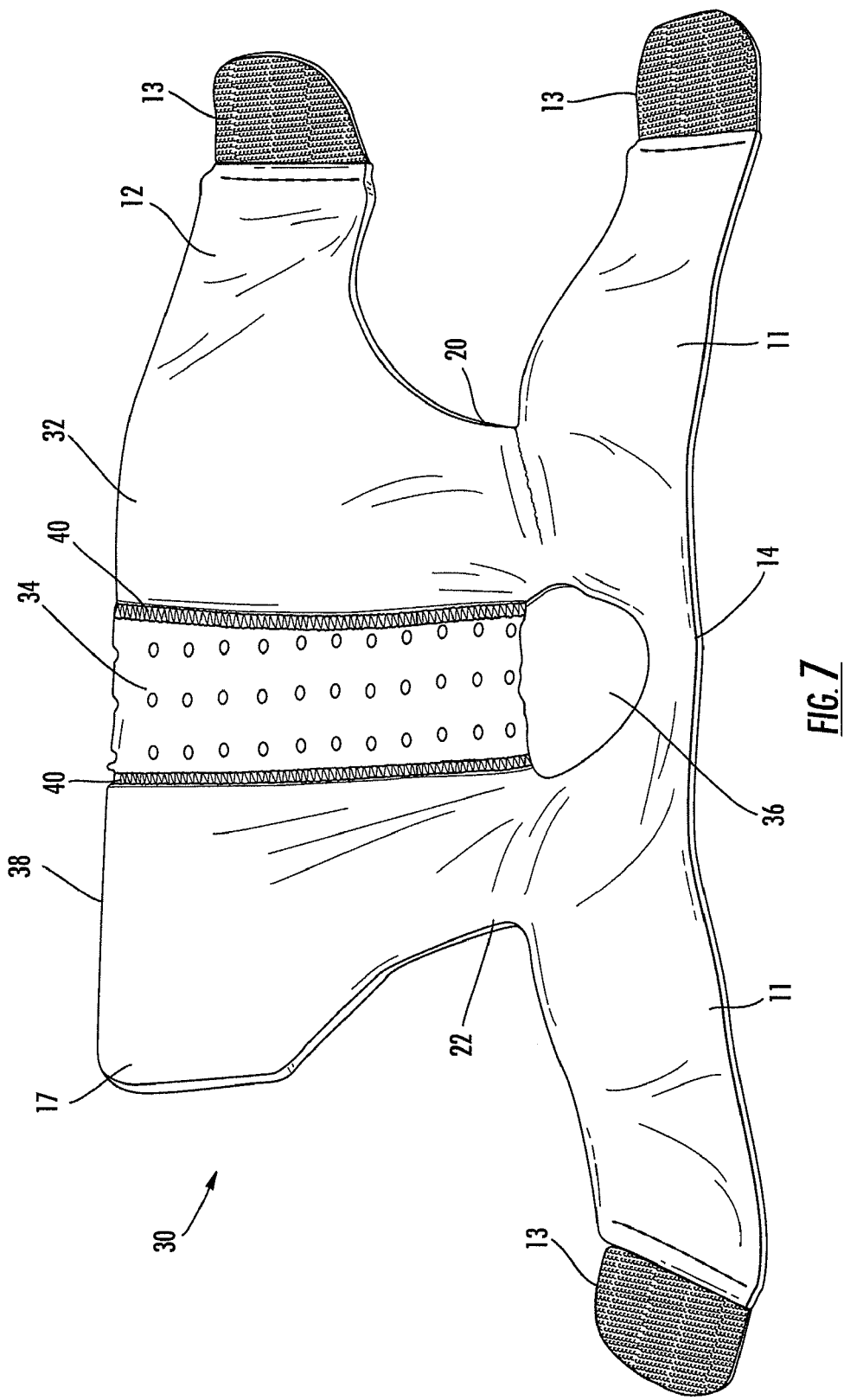
FIG. 7 is a plan view of an inner surface of an ankle support according to an additional embodiment of the present invention.
Figure 8:
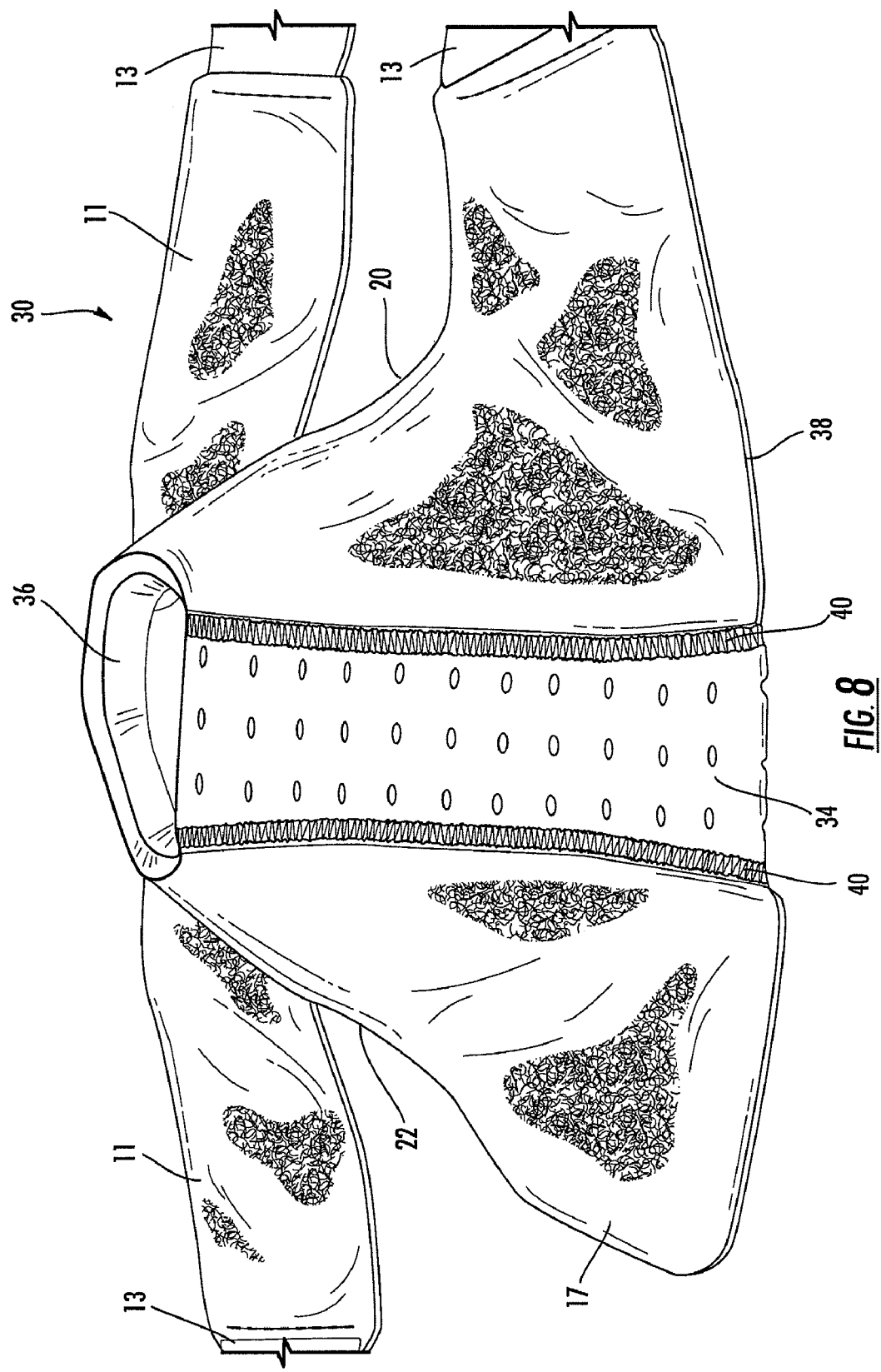
FIG. 8 is a plan view of an outer surface of the ankle support shown in FIG. 7.
Figure 9:
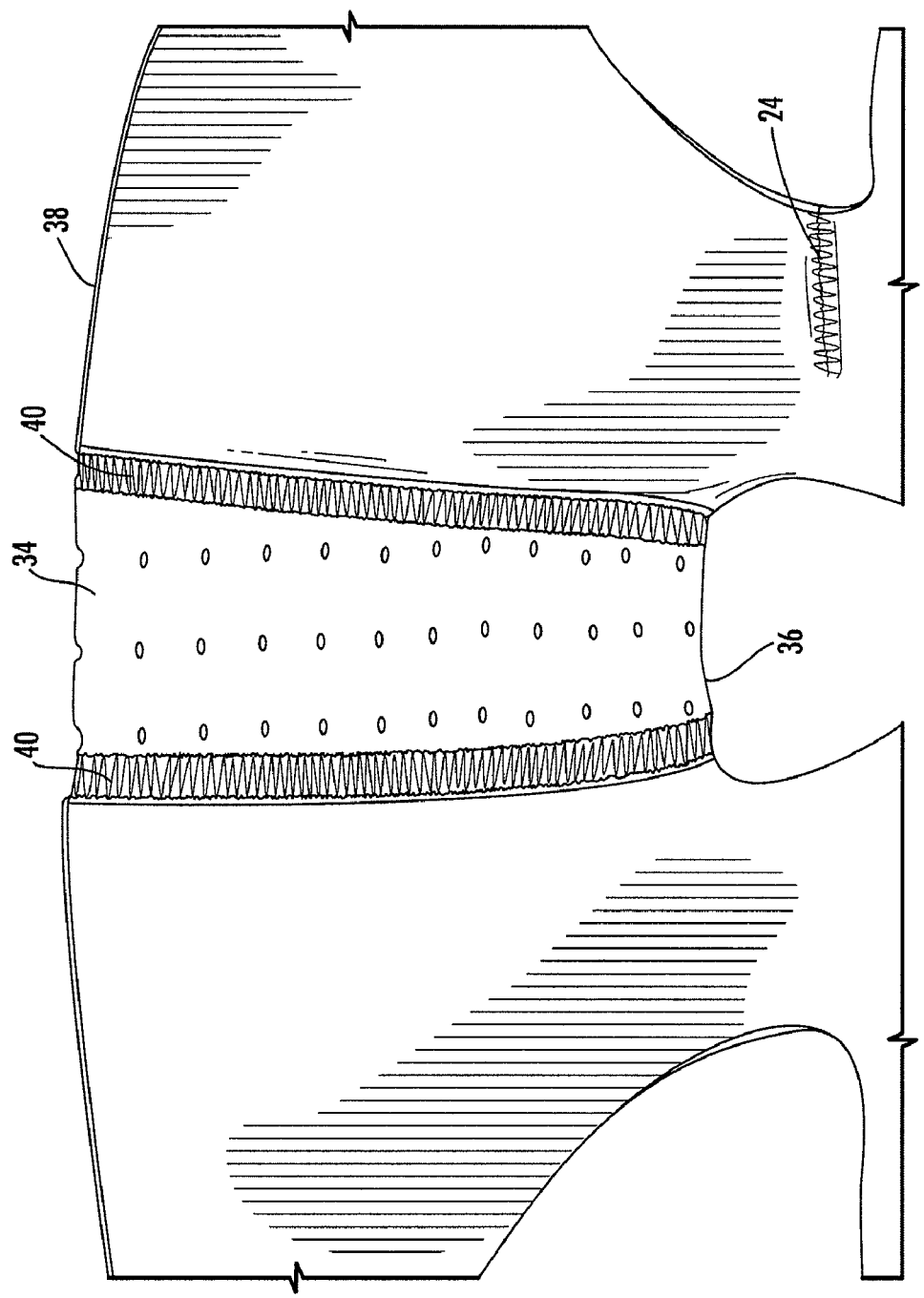
FIG. 9 is an enlarged plan view of a portion of the inner surface of the ankle support shown in FIG. 7.
Figure 10:
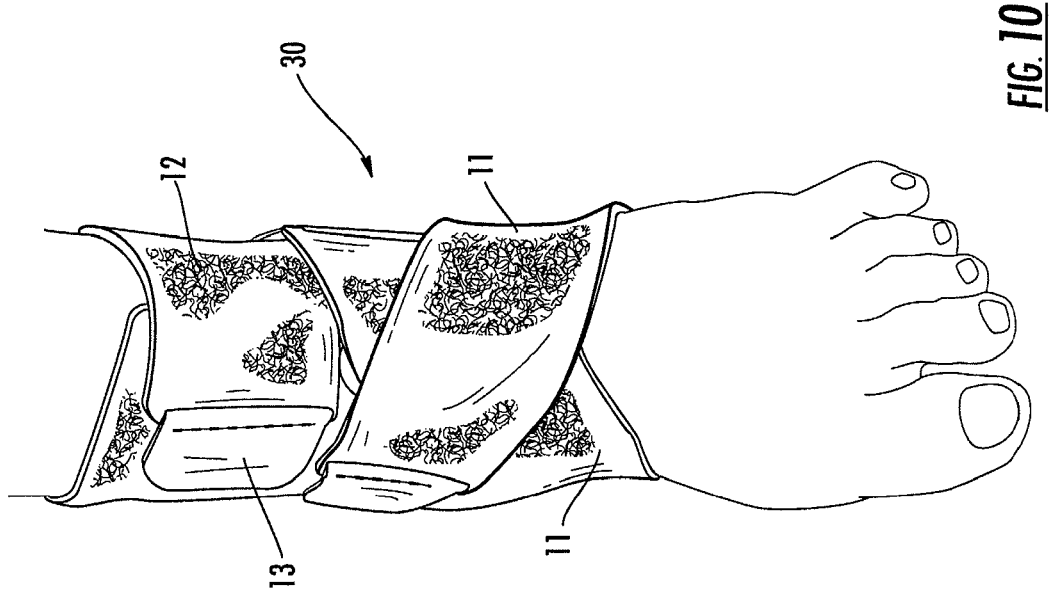
FIGS. 10 and 11 are perspective views of the ankle support shown in FIG. 7 positioned on a wearer's ankle.

In one embodiment of the present invention, shown in FIGS. 1-4, an ankle support 10 includes a single sheet of material 15 having three straps, including two opposed distal straps 11, and a single, unopposed proximal strap 12. A gap 20 is defined along a lateral edge of the sheet of material 15 between the proximal strap 12 and a distal strap 11. The opposed distal straps 11 extend upwards over the instep, cross over one another, and attach with fasteners 13 at their respective ends onto the outside of the sheet of material 15, as shown in FIGS. 5 and 6. A base portion 14 of the sheet of material 15 is configured to be positioned under the wearer's foot during use.

A tab 17 extends outwardly from a lateral edge of the sheet of material 15, where a gap 22 is defined between the tab and a distal strap 11. The tab 17 extends outward opposite the proximal strap 12 and extends under the proximal strap 12 as the strap wraps around the ankle. A wearer may grasp the tab 17 while tensioning the proximal strap 12, and the proximal strap overlaps the tab when secured to the outside of the sheet of material 15 such that the tab provides additional cushioning and support adjacent to the proximal strap.

A heel opening 16 provides space for a heel when the ankle support 10 is worn. Optionally, the ankle support 10 may include a liner that attaches to the inner surface of the sheet of material 15 and extends between the skin and the sheet of material during use to define a sleeve. For an exemplary discussion of additional or alternative configurations of the ankle support 10, see U.S. Pat. No. 6,929,617 to McCormick et al., entitled "Nonbulky Ankle Brace for Use with Footwear," and U.S. Pat. No. 6,617,485 to Herzberg, entitled "Bandage for the Ankle Joint," each of which is assigned to the present assignee and incorporated herein by reference.

In addition to its strapping structure, the body of the ankle support 10 is constructed of a single sheet of flexible laminate material 15. Two portions of the sheet of material 15 are joined together along a seam 19 that extends along the posterior portion of the wearer's lower leg, ankle, and foot during use, as shown in FIG. 3. A second seam 24 attaches portions of the sheet of material 15 together and extends from the gap 20 but stops short of the heel opening 16, as shown in FIG. 4. The seams 19 and 24 provide a contour to the sheet of material 15 so that it can correspond to the curvature of the wearer's foot and ankle. In addition, the configuration of the sheet of material 15 and seams 19 and 24 facilitate the use of a single sheet of material.

Generally, the sheet of material 15 is constructed of a laminate material having multiple plies, including a soft, skin-friendly inner layer, a foam middle layer, and a non-abrasive outer layer. The inner layer is worn against the skin and has a low skin irritant, soft feel, and moisture-wicking properties, while portions of the outer layer allows attachment of fasteners 13. In particular, the outer layer of the laminate material includes a stretch eyelet unbroken loop (e.g., style 1786 manufactured by Gehring Textiles, Inc.), as shown in FIG. 4. An inner layer of the laminate material is a stretch fleece with a grid pattern (e.g., style 9110 manufactured by Malden Mills Industries, Inc.), as shown in FIG. 3. Sandwiched between the inner and outer layers is a stretch polyurethane or polyurethane ester foam (e.g., style S0702 manufactured by Rubberlite Inc.). Although the thicknesses of the layers may vary, in one embodiment the foam layer is about 0.035 to 0.125 inches in thickness, the outer layer is about 0.007 to 0.08 inches in thickness, and the inner layer is about 0.007 to 0.10 inches in thickness. Thus, each of the layers of the laminate material are stretchable in a plurality of directions to facilitate conformability of the ankle support 10 to provide enhanced comfort and an improved fit during use. In addition, the sheet of material 15 is breathable, and the inner layer facilitates air flow along the skin surface to wick moisture away from the skin.

The seams 19 and 24 are typically formed using stitching, although other suitable attachment techniques, such as adhesives, radio-frequency welding, and the like may be used to join portions of the sheet of material 15 together. Moreover, although a single sheet of material 15 is described, the ankle support 10 could include one or more individual components that assemble together. For example, the distal 11 and proximal 12 straps could be attached to the sheet of material 15 rather than being integral with the sheet.

The outer surface of the sheet of material 15 includes a fastening material that is complementary to fastening material carried by the fasteners 13. Typically, the fastening material is constructed of a complementary hook and loop material such as VELCRO®. However, the term "fastening material," as used herein, denotes any type of chemical, mechanical, or other fastener that allows connection of two separate components, such as snaps, hook and loop connectors, adhesives, buckles, etc. Notably, the fastening material of the fasteners 13 (e.g., hooks), and the fastening material (e.g., loops) of the outer surface of the sheet of material 15 mate to, and attach with, one another when brought into contact. These fastening materials, therefore, are referred to herein as being complementary.

Figure 1:
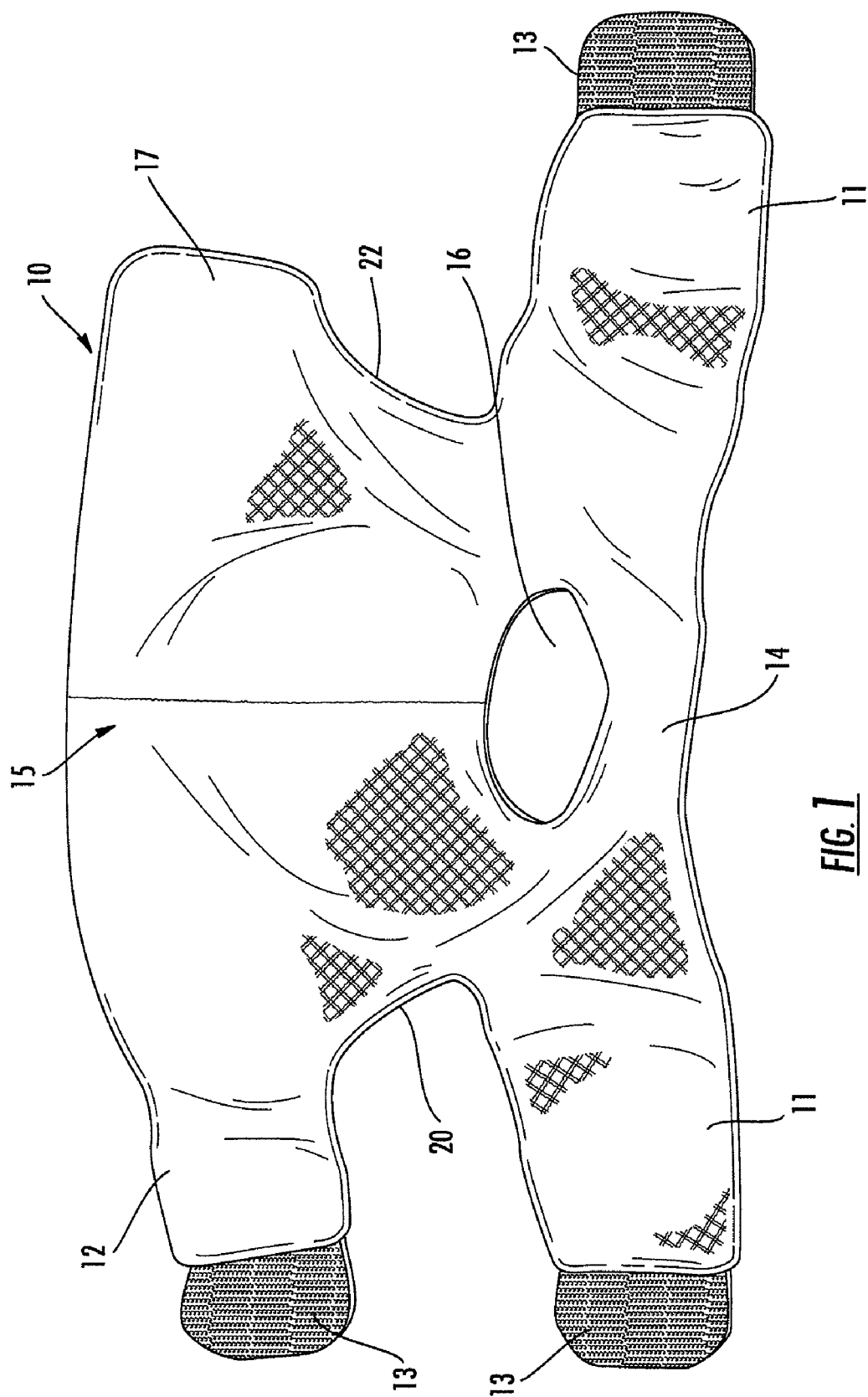
FIG. 1 is a plan view of an inner surface of an ankle support in an open configuration according to one embodiment of the present invention.
Figure 2:
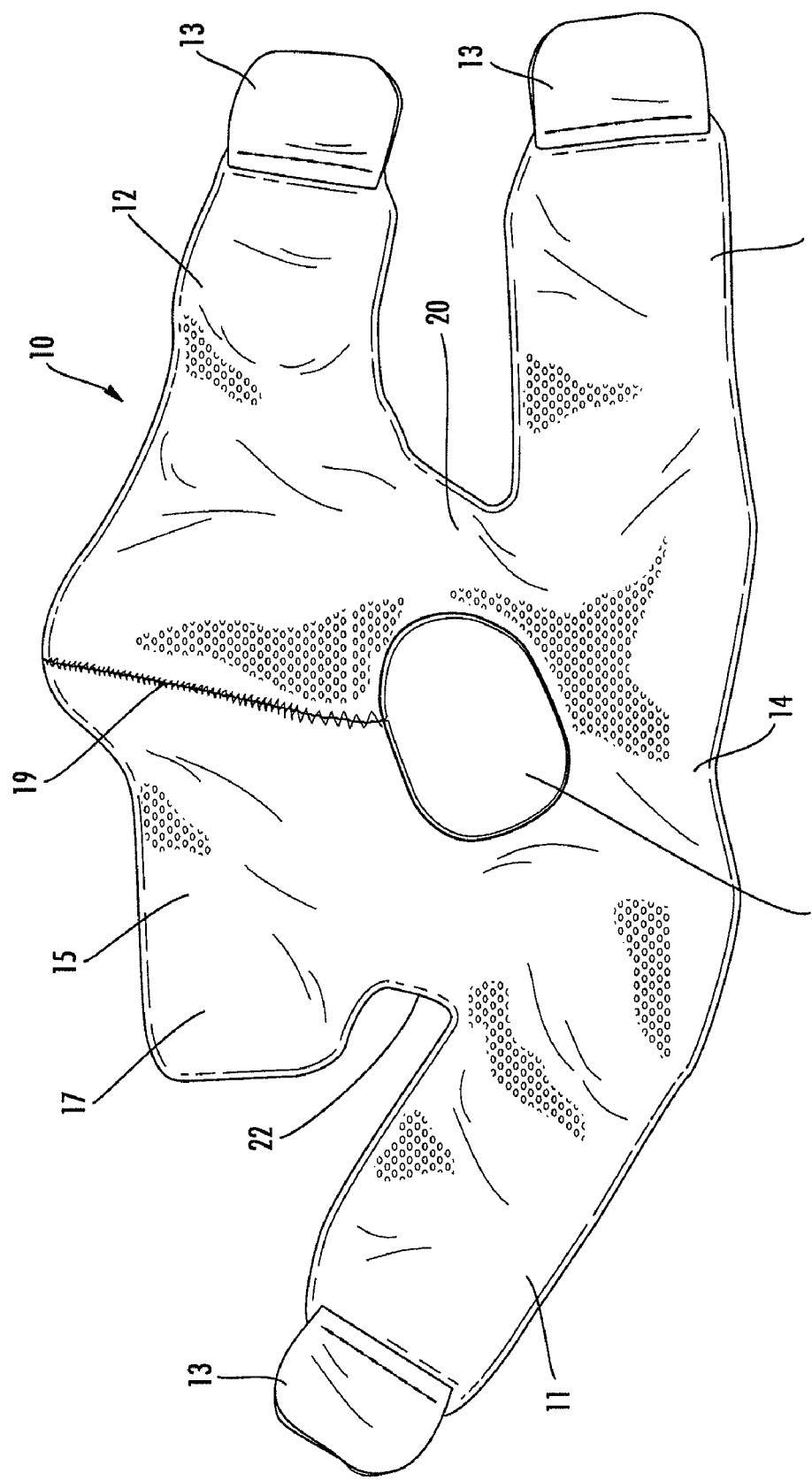
FIG. 2 is a plan view of an outer surface of the ankle support shown in FIG. 1.

During use, the wearer pulls apart the opposing edges of the sheet of material 15 to the configuration illustrated in FIG. 1, and slides his or her foot into the support until the wearer's heel extends through the heel opening 16. Meanwhile the sheet of material 15 is pulled up onto about the mid-point of the lower leg or a portion of the wearer's calf. The distal 11 straps are crossed over each other at the instep and anterior portion of the ankle. The straps 11 are pulled tight and the fastening material at the end of each of the fasteners 13 is attached to the fastening material on the outer surface of the sheet of material 15 opposite from the side of the base portion 14 on which the respective strap originated (FIGS. 5 and 6). The proximal strap 12 is extended around the anterior portion of the wearer's ankle and over the tab 17 and attached to the outer surface of the sheet of material 15 to hold the edges of the sheet of material together.

An additional embodiment of the present invention is shown in FIGS. 7-11 illustrating an ankle support 30. The ankle support 30 is similar in configuration to the ankle support 10 discussed above and includes a laminate sheet of material 32. In particular, the ankle support 30 includes a laminate material of a circular knit loop outer layer, a polyester jersey inner layer, and a layer of neoprene blend positioned therebetween. However, the sheet of material 32 could be other suitable laminate materials if desired, such as a polyurethane foam layer positioned between the inner and outer layers. Each of the materials are stretchable in multiple directions to allow the ankle support 30 to conform to various ankle sizes, as well as improve comfort during use. The outer layer is engageable by fasteners 13 secured on the ends of the distal straps 11 and proximal strap 12, such as via hook and loop materials.

Furthermore, the ankle support 30 includes a strip of spacer material 34 that extends from the heel opening 36 to a proximal edge 38. The spacer material 36 is attached to the sheet of material 32 along lateral stitch lines 40. The spacer material 36 can be various spacer materials, such as a three-dimensional spacer fabric having ridges and holes for comfort and increased breathability (e.g., style 2000 or 2001 manufactured by Malden Mills Industries, Inc.).

Figure 11:
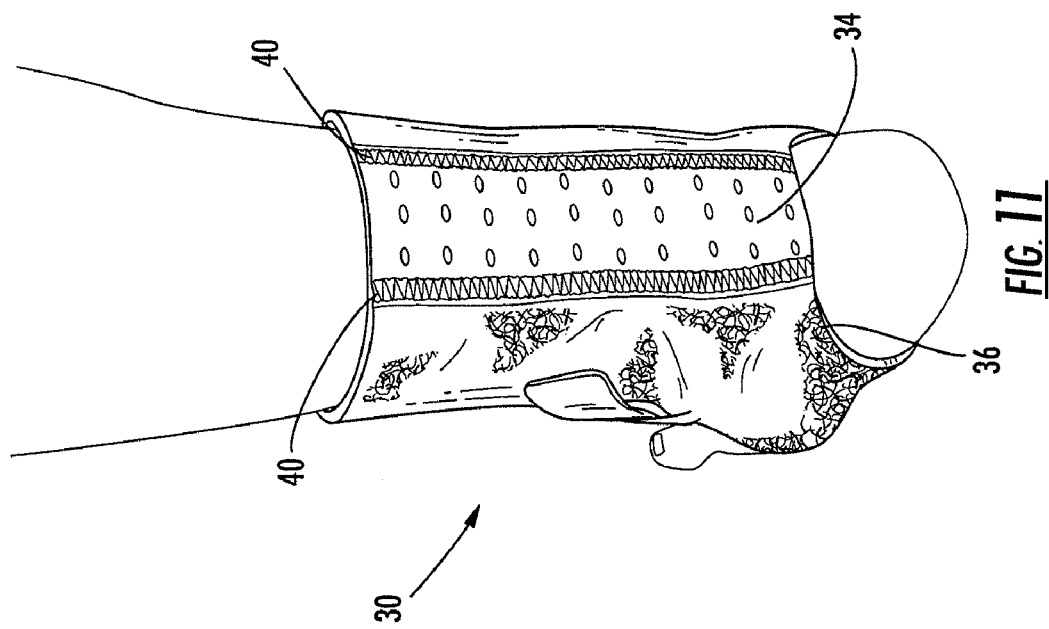
Figure 12:
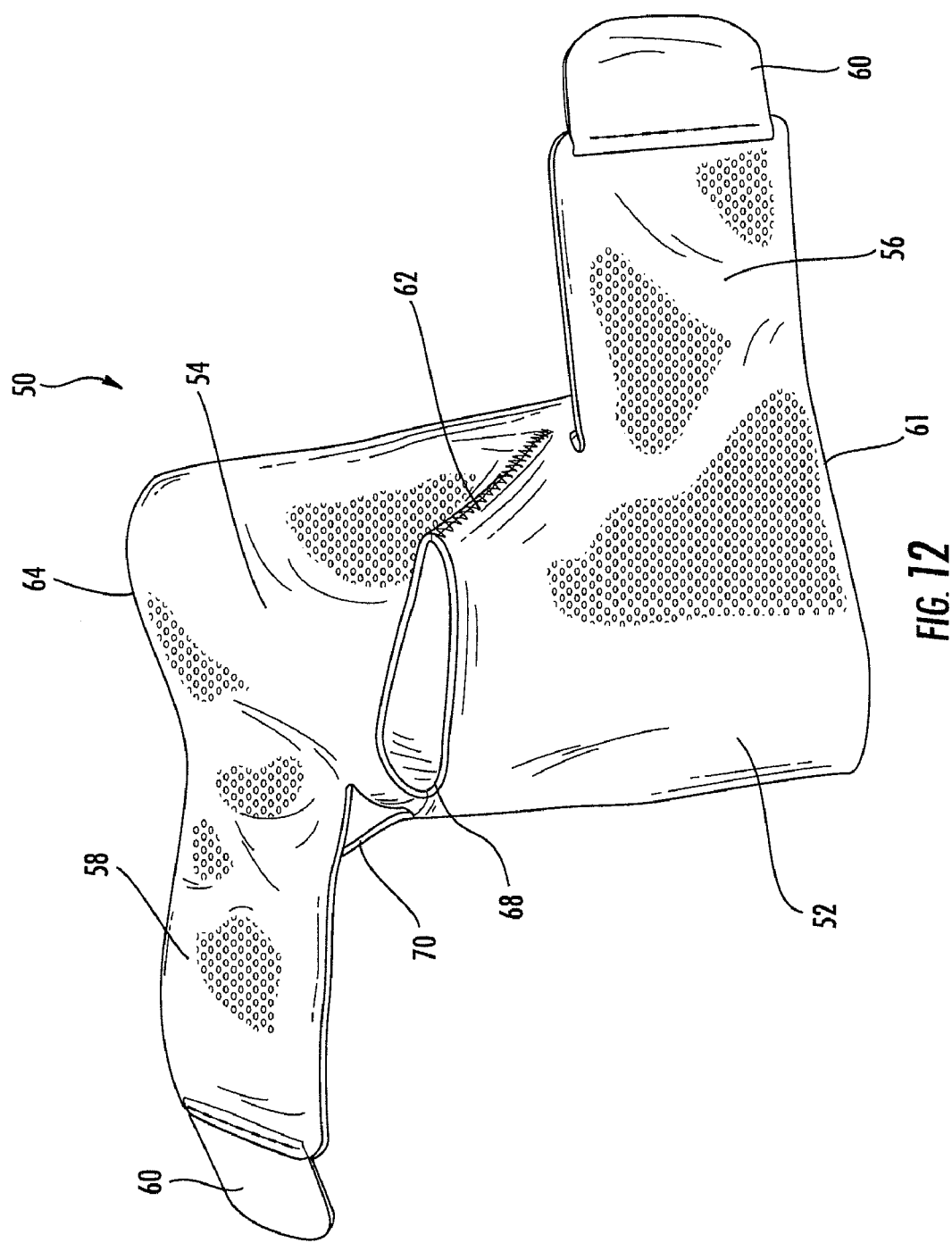
FIG. 12 is a plan view of an outer surface of an ankle support according to another embodiment of the present invention.
Figure 13:
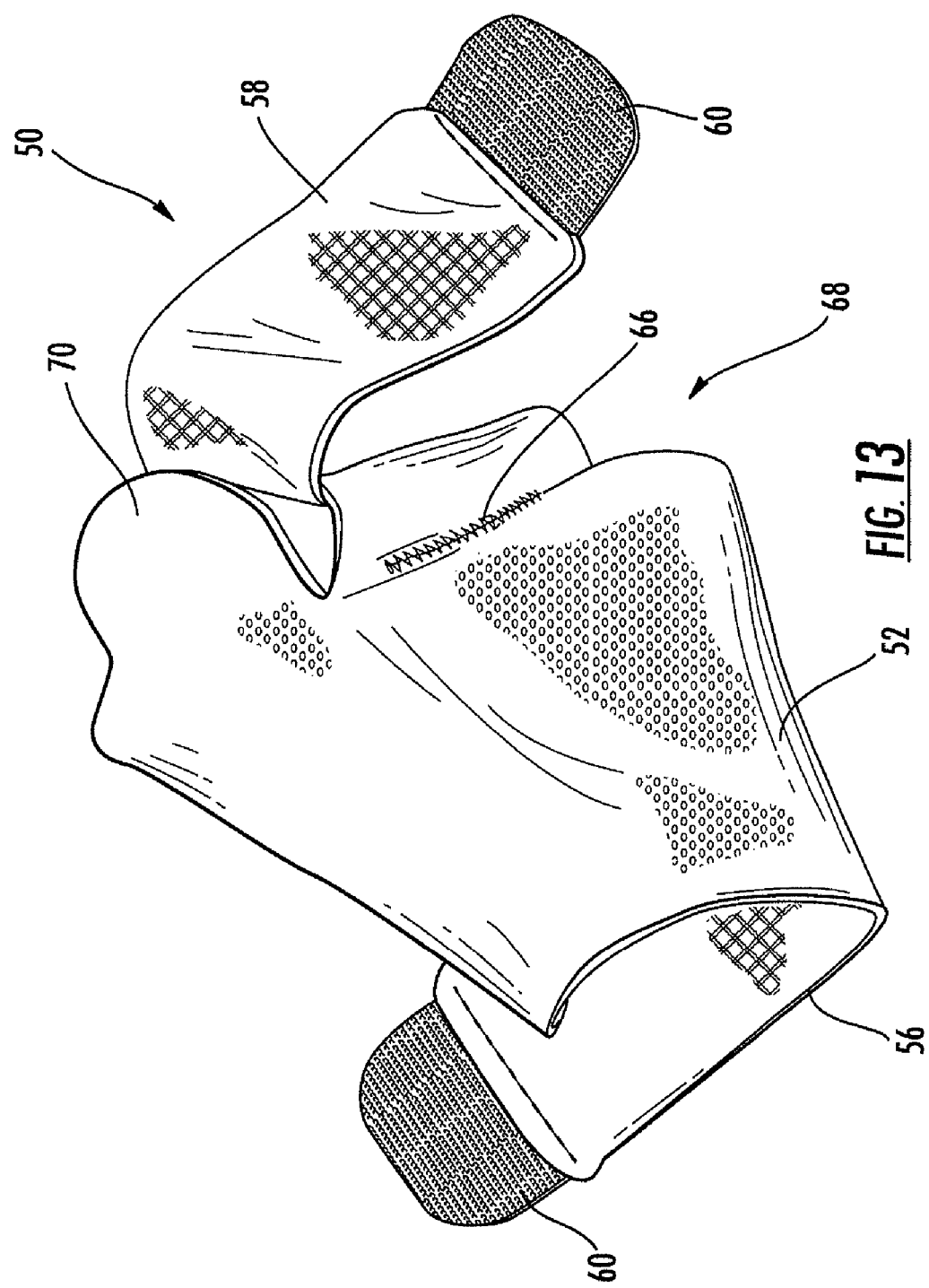
FIG. 13 is another plan view of the outer surface of the ankle support shown in FIG. 12.

Thus, during use, the spacer material 36 extends from the wearer's heel, along the Achilles tendon, and to the calf (see FIG. 11). The spacer material 36 is configured to enhance comfort and breathability without sacrificing the functionality of the ankle support 30. The spacer material 36 could be various sizes and configurations, such as about 1 to 3 inches in width and about 3 to 5 inches in length. Thus, the spacer material 36 may be various sizes and configurations for accommodating different ankle sizes and to achieve a desired amount of comfort and support. Additionally, the spacer material 36 is shown as having holes that extend through the thickness of the sheet of material 32. However, the spacer material 36 may have holes that extend at least partially through the sheet of material 32, while still enhancing breathability of the ankle support 30.

In another embodiment, as shown in FIGS. 12-16, an ankle support 50 includes a single sheet of material 52 that includes a body 54 and a pair of straps 56 and 58. In particular, the sheet of material 52 is arranged in a helical configuration with the straps 56 and 58 extending at opposite ends of the body 54. The body 54 and straps 56 and 58 are formed from a single generally rectangular sheet of material 52 that is bifurcated near its midline at opposite ends. At the distal end of the sheet of material 52, half the bifurcation is attached back to the body 54 along a distal edge 61 via a stitch line 62 and the other half extends to a distal strap 56 with a fastener 60 at its free end. At the proximal end, half the bifurcation attaches back to the body 54 along a proximal edge 64 via a second stitch line 66. The other half of the proximal bifurcation extends to a proximal strap 58 with a fastener 60.

A space between the two stitch lines 62 and 66 forms a heel opening 68. Thus, the first 62 and second 66 stitch lines extend from the heel opening 68 to a respective strap 56 and 58. Extending from the proximal edge 64 of the body 54 is a rounded instep tab 70 (see FIG. 13) that extends under the proximal strap 58 when the strap is wrapped around the ankle to secure the support 50 thereon. Similar to the tab 17 described above, the instep tab 70 facilitates positioning of the support on the wearer's ankle and tensioning of the proximal strap 58. In other words, the wearer is capable of gripping the instep tab 70 when pulling the sleeve onto the ankle and when tensioning the proximal strap 58.

As described above with respect to the ankle support 10, the ankle support 50 comprises a flexible sheet of laminate material. Therefore, the ankle support 50 includes a laminate of a stretch eyelet unbroken loop outer layer, a stretch fleece with a grid pattern inner layer, and a stretch polyurethane ester foam positioned between the inner and outer layers.

It is understood that that ankle support 50 may be various configurations to achieve a desired amount of support and comfort. For example, the distal 56 and proximal 58 straps could be various sizes and materials and, in one aspect, the distal and/or proximal strap may be omitted. For example, the ankle support 50 could include the laminate sheet of material described above (i.e., stretch eyelet unbroken loop, stretch fleece with a grid pattern, and stretch polyurethane ester foam) and configured such as that shown in FIGS. 24-30 of U.S. Patent Application Publication No. 20030050586 to Domanski et al., entitled "Orthopedic Supports," which is assigned to the present assignee and incorporated herein by reference. Alternatively, various laminate and spacer materials could be utilized for the sheet of material 52 and be configured as the body 54 and straps 56 and 58 described above. Furthermore, although the instep tab 70 is shown as being rounded, the instep tab could be various sizes and configurations, such as rectangular. In addition, although the ankle support 50 is described as being a single sheet of material 52, the ankle support could be one or more pieces of material that may be assembled together if desired.

Figure 14:
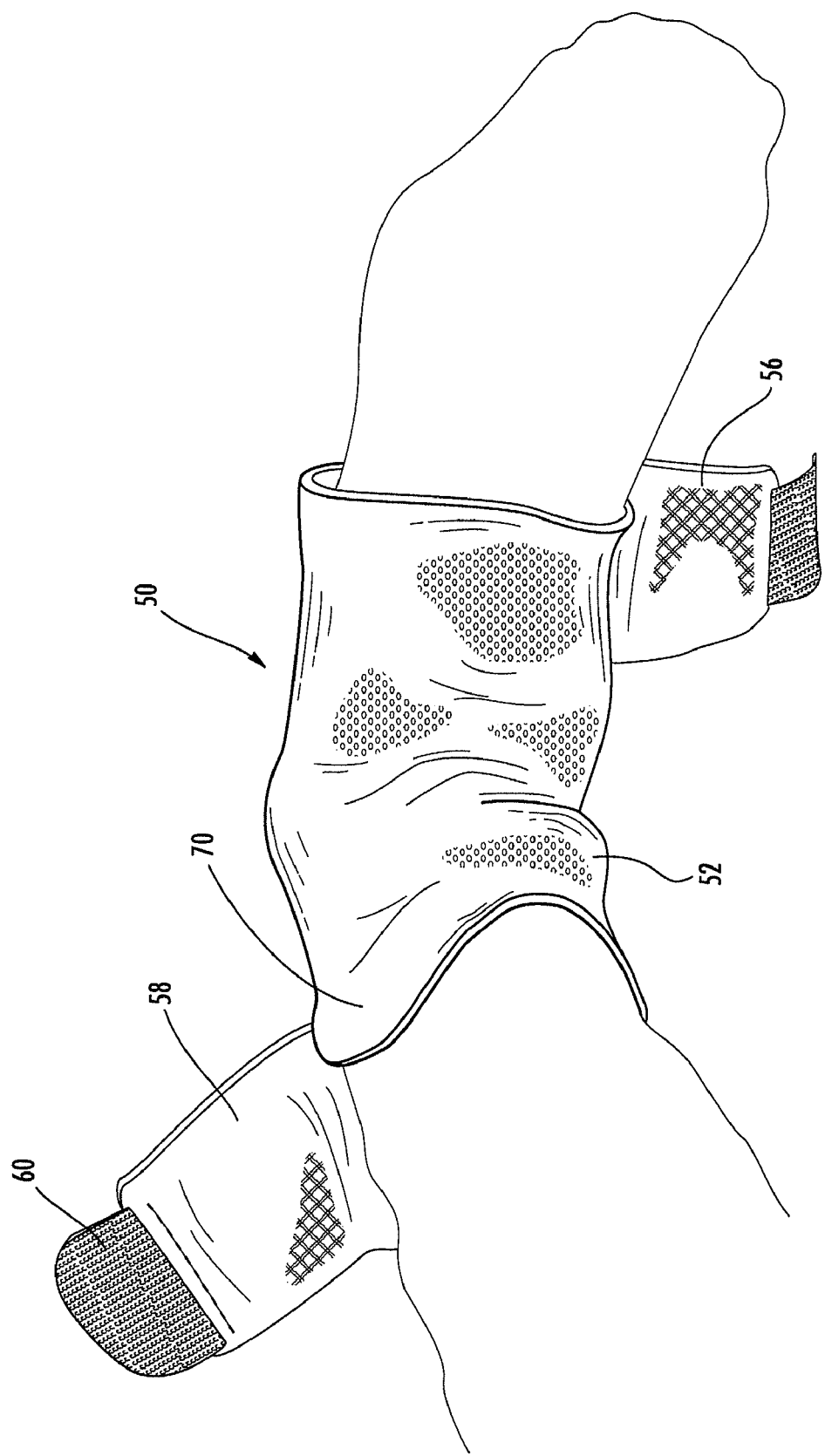
FIGS. 14-16 are perspective views of a sequence of securing the ankle support to a wearer's ankle according to one embodiment of the present invention.
Figure 15:
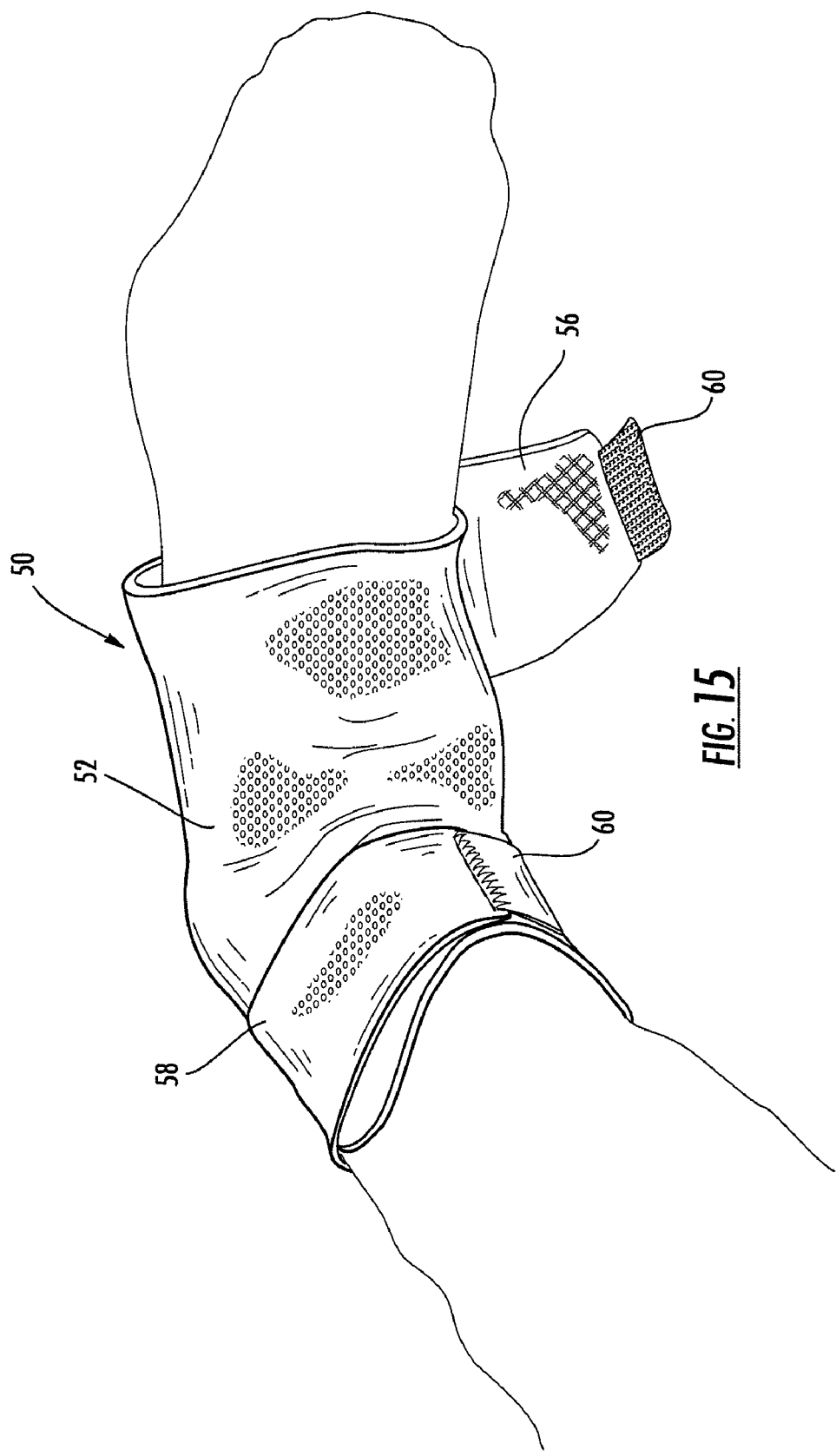
Figure 16:
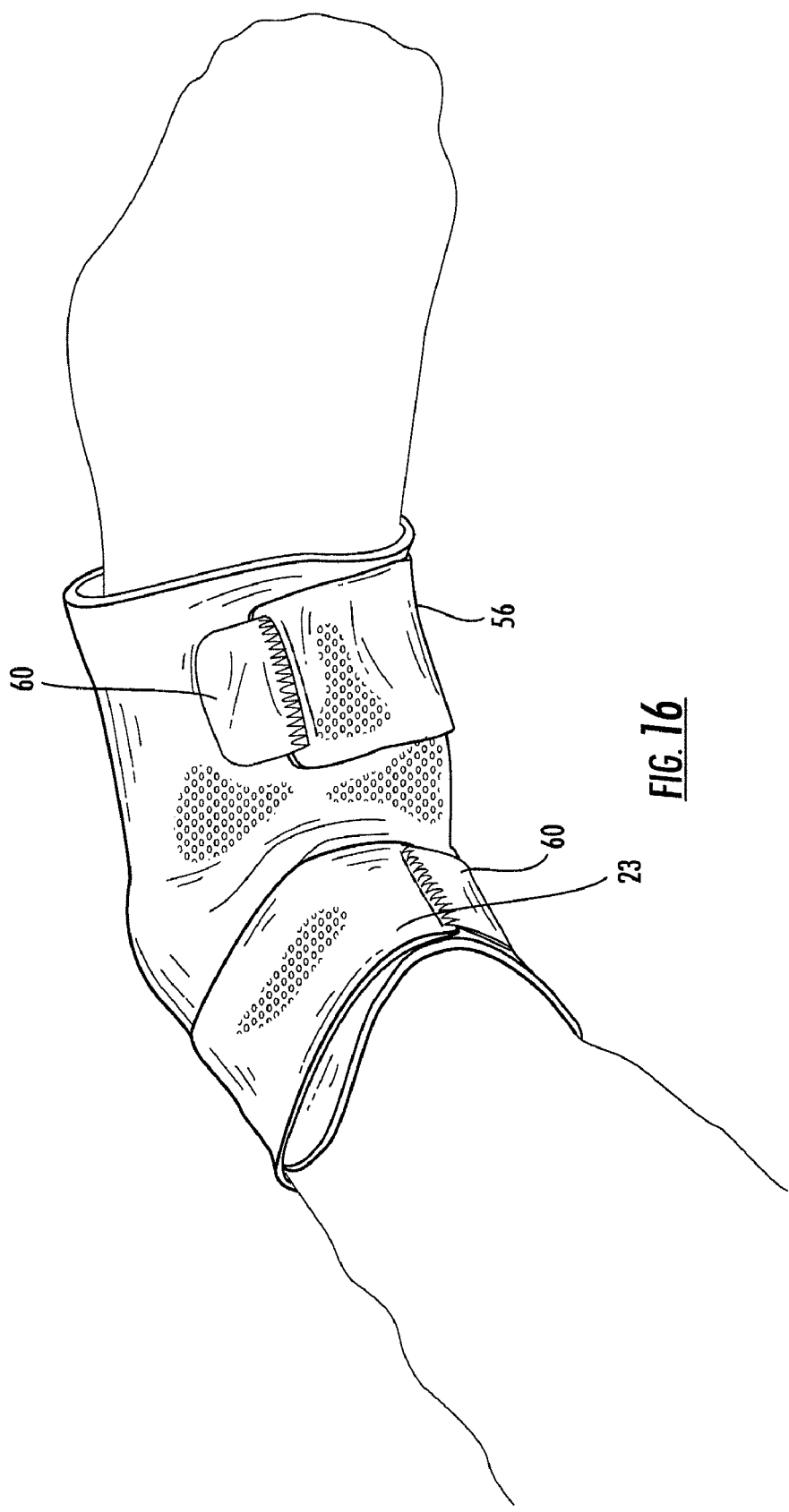

During use, the wearer pulls the body 54 of the ankle support 50 over the wearer's foot and around the wearer's ankle until the wearer's heel is positioned in the heel opening 68 (FIG. 14). The wearer may then extend the proximal strap 58 circumferentially about the ankle and over the tab 70 and secure the fastener 60 of the proximal strap to the outer surface of the body 54 (FIG. 15). The wearer could grasp the tab 70 when pulling the body 54 onto the wearer's ankle and/or while tensioning the proximal strap 58. Furthermore, the wearer may then extend the distal strap circumferentially 56 over the instep of the foot and attach the fastener 60 on the end of the distal strap to the outer surface of the body 54 (FIG. 16). Thus, the tension applied to the proximal 58 and distal 56 straps is generally directed opposite to one another.

Figure 17:
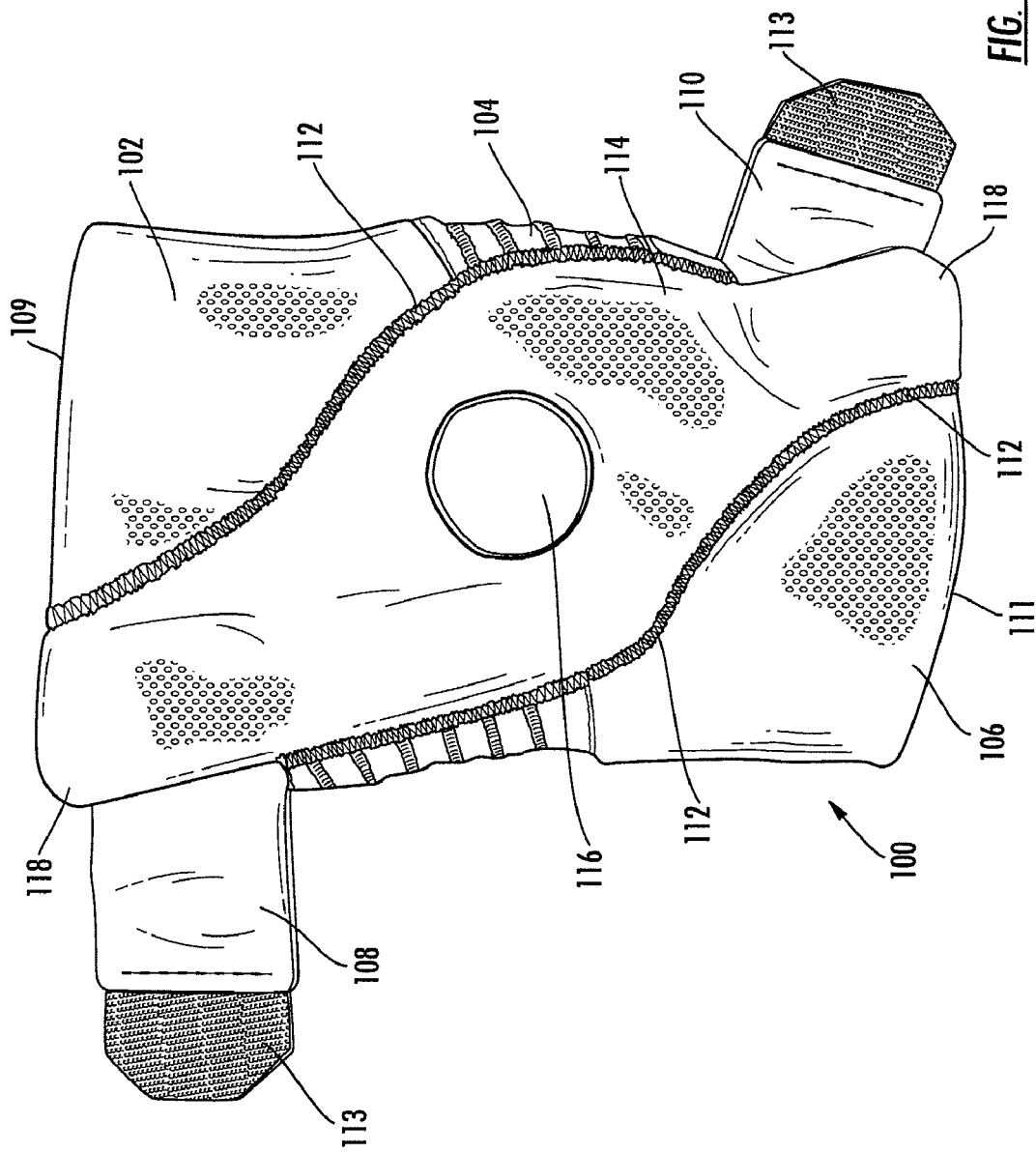
FIGS. 17 and 18 are plan views of an outer surface of a knee support according to an additional embodiment of the present invention.
Figure 18:
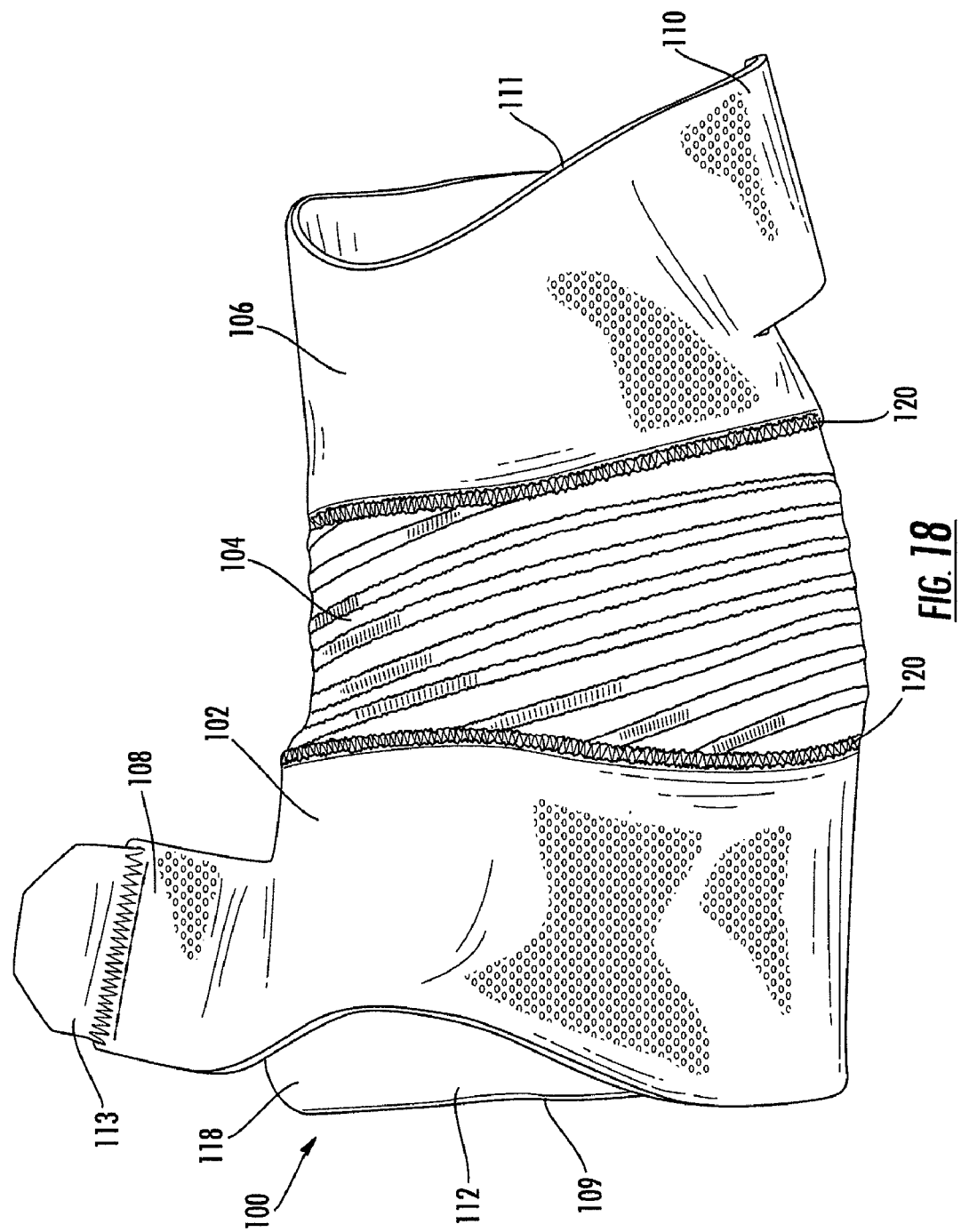
Figure 19:
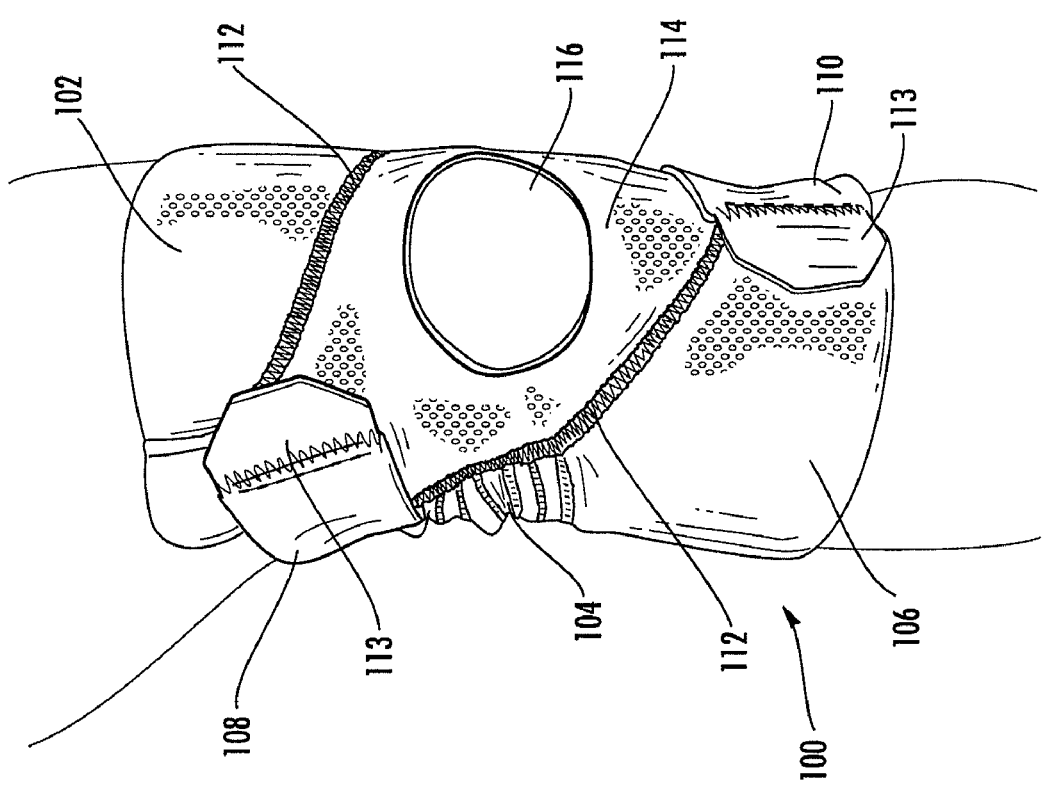
FIG. 19 is a perspective view of the knee support shown in FIGS. 17 and 18 positioned on a wearer's knee.

A further embodiment of the present invention is shown in FIGS. 17-19. In particular, FIG. 17 illustrates a spiral knee support 100. The spiral knee support 100 includes a single sheet of material comprising an upper material portion 102, a middle spacer portion 104 and a lower material portion 106 attached along lateral edges to form a sleeve. The upper portion 102 is slightly larger in diameter than the lower portion 106, as the upper portion is configured to accommodate the wearer's thigh, while the lower portion is configured to accommodate the wearer's leg below the knee.

In addition, the spiral knee support 100 includes a proximal strap 108 and a distal strap 110 that extend laterally outward in opposite directions as free end portions of the upper 102 and lower 106 material portions, respectfully. The proximal strap 108 is integrally defined in the upper portion 102 and extends along a portion of the proximal edge 109, while the distal strap 110 is integrally defined in the lower portion 106 and extends along a portion of the distal edge 111. Each of the proximal 108 and distal 110 straps includes a fastener 113 having fastening material thereon that is capable of attaching to fastening material on the outer surface of the upper portion 102, spacer portion 104, and/or lower portion 106. The proximal strap 108 is typically slightly longer than the distal strap 110 for greater adjustment proximate to the wearer's thigh.

The knee support 100 further includes two spiral stitch lines 112 that attach ends of the upper 102 and lower 106 material portions and spacer portion 104 to the lateral edges of an "eye-shaped" elastic patellar portion 114. Thus, the patellar portion 114 extends from the proximal edge 109 to the distal edge 111. Defined in the patellar portion 114 is a patellar opening 116 for accommodating the wearer's patella during use. The patellar portion 114 could be thicker than the upper 102 and lower 106 material portions to reduce the incidence of buckling around the patella.

As illustrated in FIG. 17, a tab 118 is defined in each of the proximal and distal ends of the patellar portion 114. Each tab 118 extends laterally along a portion of respective proximal 109 and distal 111 edges proximate to the proximal 108 and distal straps 110 such that the straps are capable of extending over a respective tab. The wearer could use the tabs 118 as an aid when positioning the knee support 100 or when tensioning the proximal 108 and distal 110 straps. Moreover, the tabs 118 also provide a smooth transition and increased cushioning adjacent to the straps.

Each of the upper 102 and lower 106 portions, as well as the patellar portion 114 is a laminate material. As described above with respect to the ankle supports 10 and 50, the knee support 100 comprises a sheet of laminate material including the stretch eyelet unbroken loop, stretch fleece with a grid pattern, and stretch polyurethane ester foam described above. However, the knee support 100 is capable of employing alternative laminate materials if desired, such as a laminate of polyester hook engaging loop material, a polyurethane foam, and a polyester jersey knit material, in conjunction with the configuration of the upper material portion 102, middle spacer portion 104 and lower material portion 106 described above.

According to one aspect of the knee support, the knee support 100 includes a spacer portion 104. The spacer portion 104 is typically a spacer fabric that is positioned to facilitate comfort and/or support in areas of joint bending or high friction, such as in the popliteal region of the knee. As shown in FIGS. 17 and 18, the spacer portion 104 extends circumferentially between the patellar portion 114 and the upper 102 and lower 106 material portions to correspond to the popliteal region of the wearer's knee during use. The spacer portion 104 attaches along the spiral stitch lines 112 and along upper and lower stitch lines 120. The spacer portion 104 could be various spacer materials, such as a circularly knit polyester with alternating ridges extending at an angle from horizontal (e.g., manufactured by Tytex Group) (see FIG. 18) or a three-dimensional spacer fabric (e.g., manufactured by Malden Mills Industries, Inc.). Thus, the spacer portion 104 could be elastic for facilitating bending, thicker for providing additional cushioning, and/or include a plurality of holes for providing a breathable material for areas adjacent to the wearer's skin.

It is understood that the knee support 100 may include various modifications to its size and configuration depending on the desired amount of comfort and/or support desired. For example, the proximal 108 and distal 110 straps could extend laterally in the same general direction rather than in opposite directions. The proximal 108 and distal 110 straps could also be the same length or various lengths to accommodate different knee sizes. Moreover, the knee support 100 could include a laminate material described above (i.e., stretch eyelet unbroken loop, stretch fleece with a grid pattern, and stretch polyurethane ester foam) and be a sleeve with no straps defined in the upper 102 and lower 106 portions if desired. Furthermore, although the spacer portion 104 is shown as being positioned behind the popliteal region of the knee support 100, the spacer portion could be located at various positions, such as about the entire circumference of the knee support. Additionally, although the patellar portion 114 is shown as being defined by a pair of spiral stitch lines 112, the configuration of the patellar portion could be modified to achieve various desired material properties, such as with diagonally or vertically extending stitch lines.

The knee support 100 is applied to a wearer's knee area by positioning the support such that the patella registers with the patellar opening 116, and then wrapping the straps 108 and 110 about the wearer's leg such that the proximal strap is positioned above the popliteal region of the knee and attaches to the upper portion 102, and the distal strap is positioned below the popliteal region and attaches to the lower portions 106 (see FIG. 19). The fastener 113 on the proximal strap 108 may attach to the upper portion 102 and/or a portion of the patellar portion 114, and the fastener on the distal strap 110 may attach to the lower portion 106 and/or a portion of the patellar portion. In this regard, the fastening material of the straps 108 and 110 can be adjusted to the wearer's leg size by releasably securing the fastening material to the outer surface of the upper portion 102, lower portion 106, and/or patellar portion 114.

Figure 20:
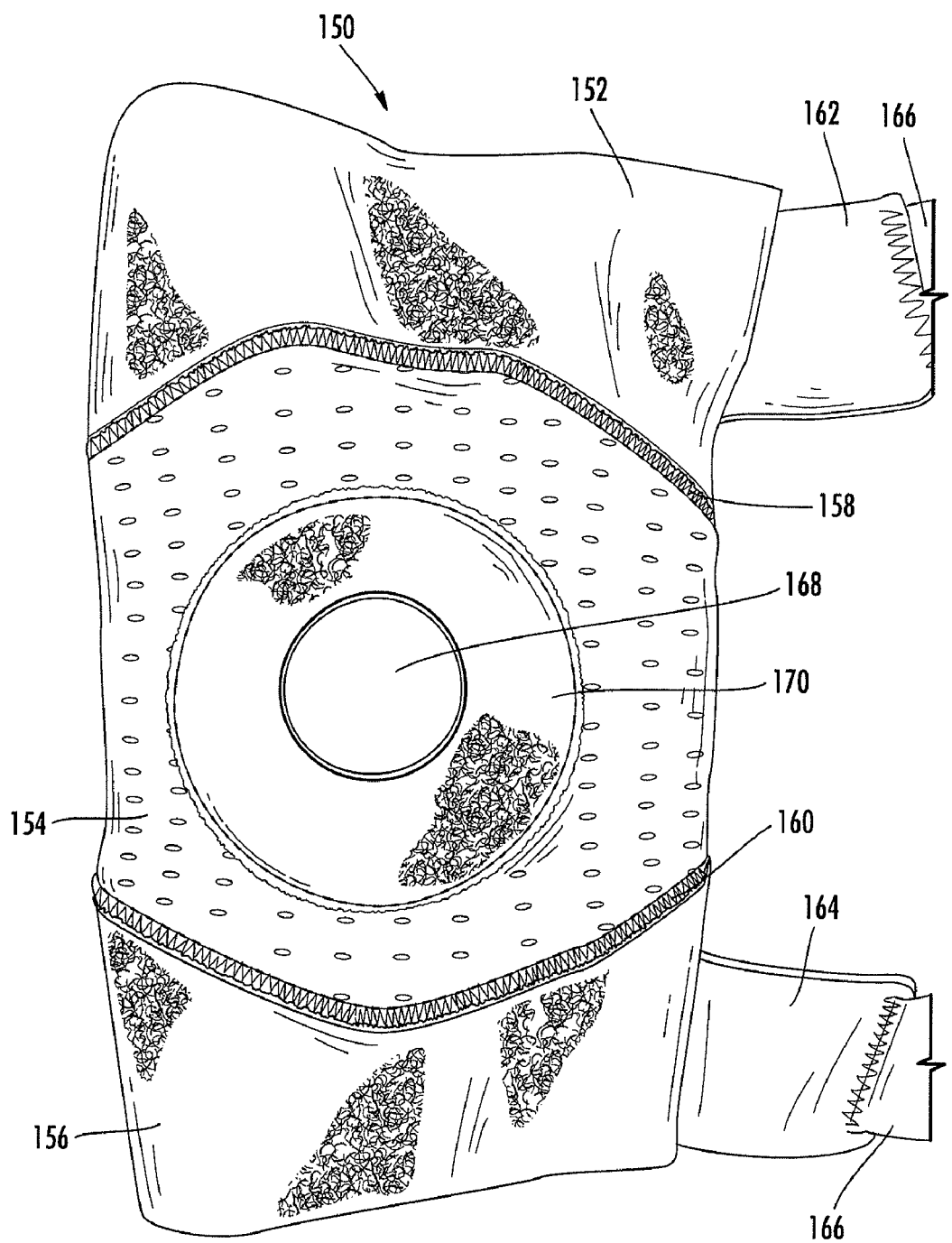
FIG. 20 is a plan view of an outer surface of a knee support according to an additional embodiment of the present invention.
Figure 21:
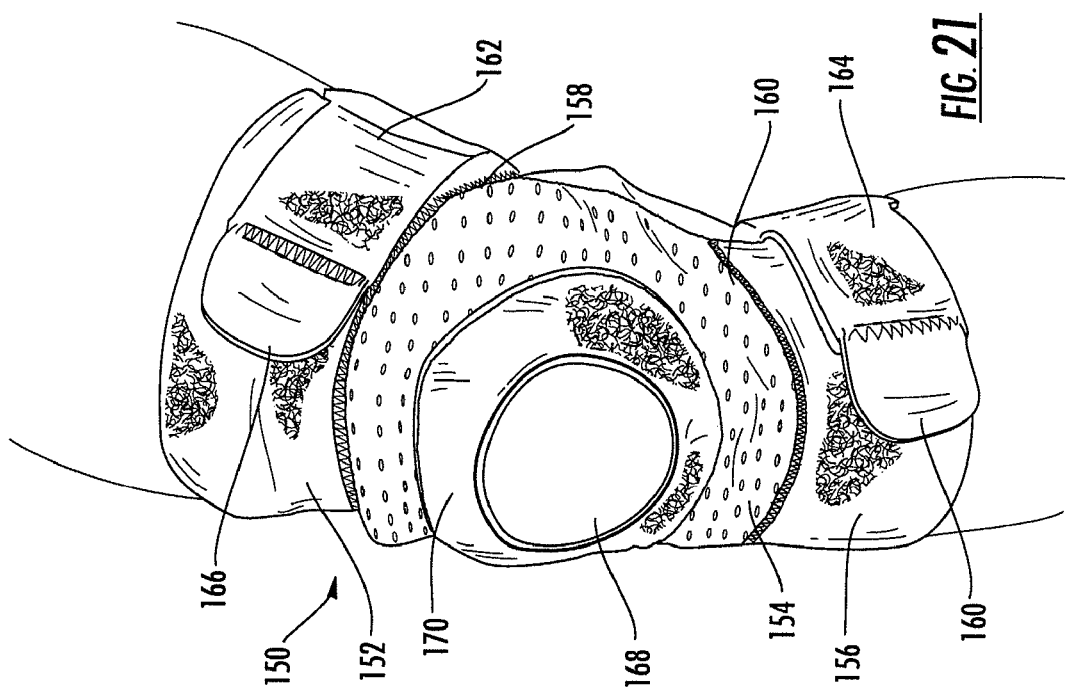
FIG. 21 is a perspective view of the knee support shown in FIG. 20 positioned on a wearer's knee.

FIGS. 20 and 21 illustrate an additional embodiment of the present invention. In particular, a knee support 150 is configured in the shape of a sleeve with a top opening and a bottom opening for accommodating the thigh and lower leg, respectively. The body of the knee support 150 includes an upper material portion 152, a middle spacer portion 154, and a lower material portion 156 attached along circumferential edges to form the sleeve. In particular, the upper portion is attached to the spacer portion 154 along an upper stitch line 158, while the lower portion 156 is attached to the spacer portion along a lower stitch line 160. The spacer portion 154 may include separate anterior and posterior portions that are attached along respective lateral edges, or the spacer portion may be a single piece of laminate material.

Defined in a front of the spacer portion 154 is a patellar opening 168. Extending around the patellar opening 168 is a stretch fabric ring 170. The fabric ring 170 is attached to the spacer portion 154 about the circumference of the fabric ring and provides additional support and padding for the wearer's patella during use. The fabric ring 170 is typically a laminate material, such as a textile/foam laminate, that provides additional cushioning proximate to the wearer's patella. For a further exemplary discussion of additional or alternative configurations and materials of the upper 152 and lower 156 portions, spacer portion 154, and fabric ring 170, see U.S. Pat. No. 6,582,382 to Domanski et al., entitled "Orthopedic Supports," which is assigned to the present assignee and incorporated herein by reference.

A portion of the ends of the upper 152 and lower 156 portions extend laterally outward to define a proximal strap 162 and a distal strap 164, respectively, wherein each strap includes a fastener 166 at its free end. Thus, the proximal 162 and distal 164 straps are integrally defined in the upper 152 and lower 156 portions, respectively. The fasteners 166 include fastening material on one surface that is complementary to fastening material on the outer surface of the upper 152 and lower 154 portions. Each of the straps 162 and 164 extend laterally outward in the same general direction and are generally parallel to one another.

It is understood that the knee support 150 may include various modifications to its size and configuration depending on the desired amount of comfort and/or support. For example, the proximal 162 and distal 164 straps could extend laterally in opposite directions, similar to that of the knee support 100. The proximal 162 and distal 164 straps could also be various lengths to accommodate different knee sizes. Moreover, the knee support 150 could include the laminate material described above with respect to each of the ankle 10 and 50 and knee 100 supports (i.e., stretch eyelet unbroken loop, stretch fleece with a grid pattern, and stretch polyurethane ester foam) and could include various spacer materials, such as those manufactured by Malden Mills Industries, Inc. An optional not shown aspect of the knee support 150 may include plastic loops or rings on the side of the knee support 150 through which the straps 162 and 164 could extend and/or loop back on itself or the outer surface of the upper 152 or lower 156 portions. Moreover, the knee support 150 could include other optional features to adjust the amount of comfort or support, such as by employing an inflatable bladder and/or flexible stays to provide bending resistance with flexion of the knee and medial/lateral support in order to support the knee area and prevent excessive movement thereof.

The knee support 150 is applied to a wearer's knee area by positioning the support such that the patella registers with the patellar opening 168, and then wrapping the straps 162 and 164 about the wearer's leg such that the proximal strap is positioned above the popliteal region of the knee and attaches to the upper portion 152, and the distal strap is positioned below the popliteal region and attaches to the lower portion 156 (see FIG. 21). In this regard, the fastening material of the straps can be adjusted to the wearer's leg size by releasably securing the fastening material to the outer surface of the upper and lower portions.

Figure 22:
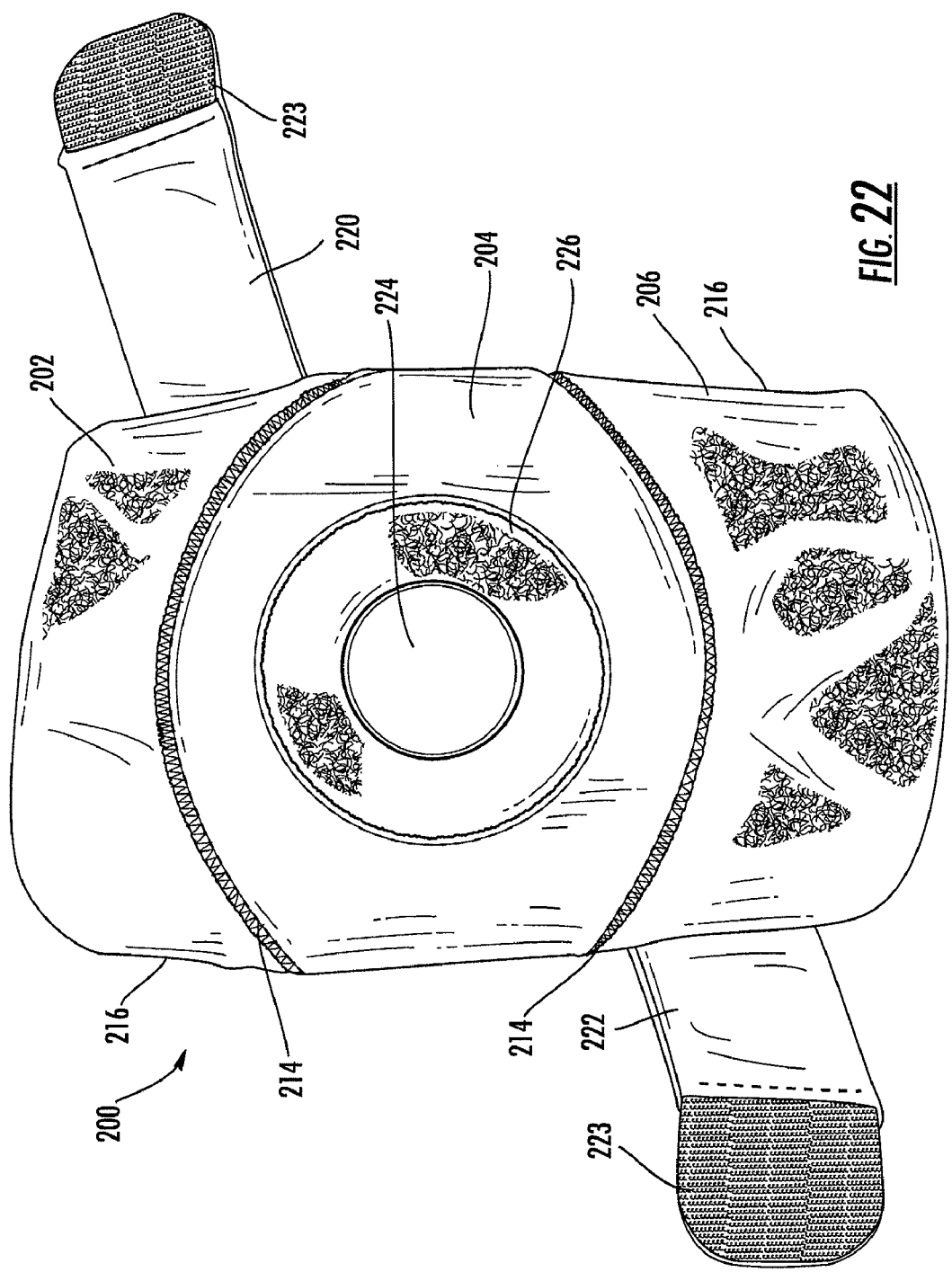
FIGS. 22 and 23 are a plan views of an outer surface of a knee support according to an additional embodiment of the present invention.
Figure 23:
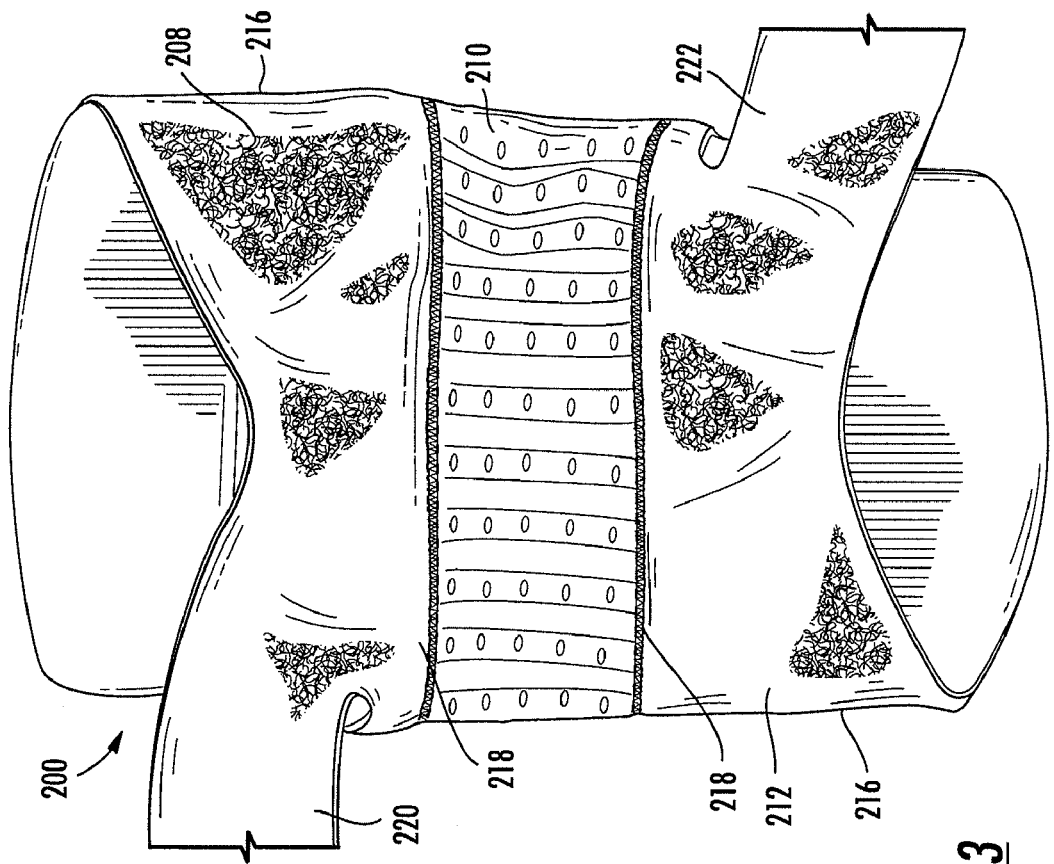

FIGS. 22 and 23 depict a knee support 200 according to an additional embodiment of the present invention. The knee support 200 is similar in configuration to the knee support 150. The knee support 200 includes an anterior upper portion 202, an anterior panel portion 204, and an anterior lower portion 206. In addition, the knee support 200 includes a posterior upper portion 208, a posterior spacer portion 210, and a posterior lower portion 212. Thus, the knee support 200 is constructed of separate anterior and posterior portions of materials. The anterior upper 202 and lower 206 portions are attached to the anterior panel portion 204 along radial stitch lines 214, while the anterior panel portion and posterior spacer portion 210 are attached along lateral stitch lines 216. The upper 208 and lower 212 posterior portions are attached to the posterior spacer portion 210 along stitch lines 218 and to the anterior upper 202 and lower 206 portions along lateral stitch lines 216. As shown in FIG. 23, the posterior upper 208 and lower 212 portions are configured to have a concave curvature that is opposite the convex curvature of the anterior upper 202 and lower 206 portions. This configuration conforms to the curvature of the knee and improves the fit of the knee support 200 during use by reducing the incidence of bunching.

Furthermore, the knee support 200 includes a proximal strap 220 and a distal strap 222 that extend in opposite directions. The proximal strap 220 is integrally defined in the posterior upper portion 208, while the distal strap 222 is integrally defined in the posterior lower portion 212. The proximal 220 and distal 222 straps are approximately parallel to one another, and the proximal strap is longer than the distal strap to accommodate the larger diameter of the thigh. For example, the proximal strap 220 could be about 3 inches in length, while the distal strap 222 could be about 2 inches in length. Each of the proximal 220 and distal 222 straps are also configured to include a concave curvature opposing the convex curvature of the anterior upper 202 and lower 206 portions, respectively. Each of the straps 220 and 222 include a fastener 223 that is engageable with the outer surface of the anterior upper 202 and lower 206 portions, respectively, such as via hook and loop fasteners. In addition, unlike conventional knee sleeves, the proximal 220 and distal 222 straps further secure the knee support 200 on the wearer's knee, while also allowing the wearer to adjust the amount of tension applied to the straps.

The anterior panel portion 204 includes a patellar opening 224 for accommodating the wearer's patella during use (see FIG. 24). The anterior panel portion 204 also includes a fabric ring 226 that is attached about its outer circumference to the anterior panel portion and about its inner circumference along the patellar opening 224. The fabric ring 226 provides additional cushioning about the circumference of the wearer's patella The anterior panel portion 204 is typically a flexible and stretchable material such as a laminate including a neoprene blend material sandwiched between layers of polyester jersey material, but could also be other suitable materials such as a spacer material (e.g., style 2000 or 2001 manufactured by Malden Mills Industries, Inc.). The posterior spacer portion 210 can be various spacer materials, such as a three-dimensional spacer fabric having ridges and holes for comfort and increased breathability (e.g., style 2000 or 2001 manufactured by Malden Mills Industries, Inc.). The upper and lower portions, as well as the fabric ring are typically a laminate of an outer layer of circular knit loop material, an inner layer of polyester jersey material, and a layer of neoprene blend material positioned therebetween. Each of the materials are stretchable in multiple directions to allow the knee support 200 to conform to various knee sizes, as well as improve comfort during use.

It is understood that the knee support 200 may include various modifications according to additional aspects of the present invention. For example, the proximal 220 and distal 222 straps may be various sizes and configurations and may even be the same length if desired. As is also understood, the thicknesses of each of the components, such as the anterior panel portion 204, can be modified to vary the amount of support and comfort of the knee support 200. Furthermore, although the knee support 200 is shown as having anterior upper 202 and lower 206 portions, as well as posterior upper 208 and lower 212 portions, the respective anterior and posterior portions may be a uniform piece of material if desired. Similarly, the anterior panel portion 204 could be a spacer material such that spacer material extends about the entire circumference of the knee support 200 and could also, or alternatively, be uniform with the posterior spacer portion 210. Furthermore, although stitching is shown as attaching each of the components of the knee support 200 to one another, various techniques, such as adhesives and radiofrequency welding could alternatively be employed. Additionally, the posterior spacer portion 210 is shown as having holes that extend through its entire thickness. However, the posterior spacer portion 210 may have holes that extend at least partially through the material, while still enhancing breathability of the material.

The present invention has many advantages. For instance, the orthopedic supports provide a unique combination of materials that promote increased comfort and moisture-wicking properties. In particular, each of the materials is stretchable, which allows the support to conform to various limb sizes, as well as breathable for wicking moisture away from the skin to provide increased comfort over prolonged periods of use. The orthopedic support may incorporate spacer materials to provide further comfort in the areas of joint bending, such as in the popliteal region of the knee. Furthermore, the orthopedic supports are capable of being configured for supporting a variety of limbs, such as the knee and ankle, and include unique strapping configurations for securing each support to the wearer's limb. In addition, the supports may be formed from a single sheet of material, which reduces the time and the number of components required for assembly.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An orthopedic support comprising:
   a single sheet of flexible laminate material including two opposed distal straps and a single, unopposed proximal strap with a gap defined along a lateral edge of the single sheet of flexible laminate material between the proximal strap and one of the two opposed distal straps, the single sheet of flexible laminate material configured to extend about and conform to a joint of a wearer;
   a spacer material attached to the single sheet of flexible laminate material about at least a portion of its outer periphery,
   wherein at least one of the two opposed distal straps and the single, unopposed proximal strap is configured to tension and secure the single sheet of flexible laminate material about the wearer's joint.

2. The orthopedic support according to claim 1, wherein the single sheet of flexible laminate material comprises a circular knit loop outer layer, a polyester jersey inner layer, and a neoprene blend positioned between the outer and inner layers.

3. The orthopedic support according to claim 1, wherein the spacer material comprises a three-dimensional knit fabric having a plurality of ridges and holes defined therein.

4. The orthopedic support according to claim 3, wherein the plurality of holes extend at least partially through a thickness of the single sheet of flexible laminate material.

5. The orthopedic support according to claim 1, wherein the spacer material is configured to align with a popliteal region of a wearer's knee.

6. The orthopedic support according to claim 1, wherein the spacer material is configured to align with an Achilles region of a wearer's ankle.

7. The orthopedic support according to claim 6, further comprising a heel opening defined in the single sheet of flexible laminate material, wherein the spacer material extends from the heel opening to a proximal edge of the single sheet of flexible laminate material.

8. The orthopedic support according to claim 1, wherein the single, unopposed proximal strap and one of the two opposed distal straps extend laterally in opposite directions.

9. The orthopedic support according to claim 1, wherein at least a portion of opposed lateral edges of the single sheet of flexible laminate material are attached to define a sleeve.

10. The orthopedic support according to claim 1, further comprising a patellar opening defined in the single sheet of flexible laminate material and configured for accommodating a patella of the wearer.

11. The orthopedic support according to claim 10, wherein the single sheet of flexible laminate material further comprises a laminate fabric ring extending about the circumference of the patellar opening.

12. The orthopedic support according to claim 11, wherein the single sheet of flexible laminate material further comprises a laminate of cushioning material extending adjacent to the laminate fabric ring and about the circumference of the patellar opening.

13. The orthopedic support according to claim 11, wherein the spacer material extends between lateral edges of the laminate fabric ring.

14. The orthopedic support according to claim 1, wherein the single sheet of flexible laminate material and spacer material are approximately the same thickness.

15. An orthopedic support comprising:
- a single sheet of flexible laminate material including two opposed distal straps and a single, unopposed proximal strap with a gap defined along a lateral edge of the single sheet of flexible laminate material between the proximal strap and one of the two opposed distal straps, the single sheet of flexible laminate material configured to extend about and conform to a joint of a wearer's anatomy;
- a spacer material attached to the single sheet of flexible laminate material about at least a portion of its outer periphery, wherein the spacer material is configured to extend partially about a circumference of the joint such that the spacer material aligns with a posterior region of the joint,
- wherein at least one of the two opposed distal straps and the single, unopposed proximal strap is configured to tension and secure the single sheet of material about the joint.

16. The orthopedic support according to claim 15, wherein the spacer material is configured to align with a popliteal region of a wearer's knee.

17. The orthopedic support according to claim 15, wherein the spacer material is configured to align with an Achilles region of a wearer's ankle.

18. The orthopedic support according to claim 15, wherein the single sheet of flexible laminate material and spacer material are approximately the same thickness.

19. A method for securing an orthopedic support about a joint of a wearer comprising:
- positioning a single sheet of flexible laminate material about a joint of a wearer, the single sheet of flexible laminate material including two opposed distal straps and a single, unopposed proximal strap with a gap defined along a lateral edge of the single sheet of flexible laminate material between the proximal strap and one of the two opposed distal straps;
- aligning a spacer material with a posterior region of the joint, wherein the spacer material is attached to the single sheet of flexible laminate material about at least a portion of its outer periphery and extends partially about a circumference of a portion of the joint; and
- tensioning at least one of the two opposed distal straps and the single, unopposed proximal strap to secure the single sheet of flexible laminate material about the joint.

20. The method according to claim 19, wherein aligning comprises aligning the spacer material with a popliteal region of a wearer's knee.

21. The method according to claim 19, wherein aligning comprises aligning the spacer material with the Achilles region of the wearer's ankle.

* * * * *